US010370638B2

(12) United States Patent
Takebe et al.

(10) Patent No.: US 10,370,638 B2
(45) Date of Patent: Aug. 6, 2019

(54) PRIMITIVE GUT ENDODERM CELLS AND METHOD FOR PRODUCING SAME

(71) Applicant: PUBLIC UNIVERSITY CORPORATION YOKOHAMA CITY UNIVERSITY, Yokohama-shi, Kanagawa (JP)

(72) Inventors: Takanori Takebe, Yokohama (JP); Hideki Taniguchi, Yokohama (JP); Ran ran Zhang, Yokohama (JP)

(73) Assignee: PUBLIC UNIVERSITY CORPORATION YOKOHAMA CITY UNIVERSITY, Yokohama-Shi (JP)

(*) Notice: Subject to any disclaimer, the term of this patent is extended or adjusted under 35 U.S.C. 154(b) by 94 days.

(21) Appl. No.: 15/534,205

(22) PCT Filed: Dec. 8, 2015

(86) PCT No.: PCT/JP2015/084379
§ 371 (c)(1),
(2) Date: Jun. 8, 2017

(87) PCT Pub. No.: WO2016/093222
PCT Pub. Date: Jun. 16, 2016

(65) Prior Publication Data

US 2017/0335277 A1 Nov. 23, 2017

(30) Foreign Application Priority Data

Dec. 9, 2014 (JP) ................................ 2014-248694

(51) Int. Cl.
*C12N 5/074* (2010.01)
*C12N 5/10* (2006.01)
*A01N 1/02* (2006.01)

(52) U.S. Cl.
CPC ............ *C12N 5/0607* (2013.01); *A01N 1/02* (2013.01); *C12N 5/10* (2013.01); *C12N 2501/115* (2013.01); *C12N 2501/155* (2013.01); *C12N 2501/16* (2013.01); *C12N 2501/165* (2013.01); *C12N 2501/415* (2013.01); *C12N 2501/727* (2013.01); *C12N 2506/45* (2013.01)

(58) Field of Classification Search
CPC .. C12N 5/0607; C12N 5/10; C12N 2501/115; C12N 2501/155; C12N 2501/16; C12N 2501/165; C12N 2501/415; C12N 2501/727; C12N 2506/45; A01N 1/02
See application file for complete search history.

(56) References Cited

U.S. PATENT DOCUMENTS

2014/0329321 A1 11/2014 Rajesh et al.

FOREIGN PATENT DOCUMENTS

WO WO 2013/174794 A1 11/2013

OTHER PUBLICATIONS

NIH (Stem Cells: Scientific Progress and Future Research Directions, Department of Health and Human Services, Chapter 1, pp. 1-4, Jun. 2001).*
Jaenisch et al., Cell, 132: 567-582, 2008.*
Zorn et al., Annu. Rev. Cell. Dev. Biol., 25: 221-251, 2009.*
Kaestner, Cell Cycle, 9(4): 634-35, 2010.*
Yanagida et al., PLoS One, 8(7), e67541:1-15, 2013.*
Cao et al., J. of Exp. Zoo., 311A: 368-376, 2009.*
Brevini et al., Theriogenology, 74: 544-550, 2010.*
Paris et al., Theriogenology, 74: 516-524, 2010.*
Munoz et al., Theriogenology, (69): 1159-1164, 2008.*
Gomez et al., Theriogenology, (74): 498-515, 2010.*
Jean et al. Develop. Growth Differ., (55): 41-51, 2013.*
Li et al., Blood, 98: 335-342, 2001.*
Wobus et al. (1997) J MoL Cell Cardiology 29:1525.*
Xu et al. (2002) Circulation Research 91:50t.*
Wobus et al. (1988) Biomed. Biochim Acta 12:965.*
Schuldiner (2000) PNAS 97:11307.*
Johansson et al. (1995) Mol and Cell Biol. 15:141.*
Feng et al., Journal of Medicinal Chemistry, 59, 2269-2300, 2016.*
Li et al., BioResearch Open Access, 1(5), pp. 205-214, 2012.*
Extended European Search Report dated May 11, 2018, in European Patent Application No. 15868455.5.
Takebe et al., "Vascularized and functional human liver from a iPSC-derived organ bud transplant," Nature (Jan. 2013), pp. 1-5.
Takebe et al., "Generation of a vascularized and functional human liver from an iPSC-derived organ bud transplant," Nature Protocols (Jan. 2014), vol. 9, No. 2, pp. 396-409.
Zhang et al., Identification of Proliferating Human Hepatic Cells From Human Induced Pluripotent Stem Cells, Transplantation Proceedings (May 2014), vol. 46, No. 4, pp. 1201-1204.
Hassani et al., "Inhibition of TGFβ Signaling Promotes Ground State Pluripotency", Stem Cell Reviews and Reports, 2014, vol. 10, pp. 16-30.
International Search Report issued in PCT/JP2015/084379 (PCT/ISA/210), dated Mar. 15, 2016.

(Continued)

*Primary Examiner* — Thaian N Ton
(74) *Attorney, Agent, or Firm* — Birch, Stewart, Kolasch & Birch, LLP

(57) ABSTRACT

The present invention provides a technique that serves as a platform for inducing human organ cells at a low cost, stably and in a large quantity. A cell inducible after differentiating pluripotent stem cells and then passaging the resultant cells at least once or more times, which is negative for undifferentiated (pluripotent) cell markers NANOG, OCT4, MYC and LIN28A, negative for endoderm cell markers CXCR4, CER1, HHEX and GATA4, positive for intestinal endoderm cell markers CDX2 and HOXB9, negative for a mesenchymal cell marker brachyury (T), negative for a pancreatic cell marker PDX1, and capable of differentiating into at least a hepatocyte, a pancreatic cell and an intestinal cell. Also provided are methods of preparing and amplifying the above cells; a method of preparing organ cells using the above cells; and a method of constructing a working cell bank for preparing organ cells, comprising cryopreserving the above cells.

5 Claims, 29 Drawing Sheets
(26 of 29 Drawing Sheet(s) Filed in Color)

(56) References Cited

OTHER PUBLICATIONS

Takebe et al., "Human iPSC-Derived Miniature Organs: A Tool for Drug Studies", Clinical Pharmacology & Therapeutics, Sep. 2014, vol. 96, No. 3, pp. 310-313.
Wang et al., "Targeting SOX17 in Human Embryonic Stem Cells Creates Unique Strategies for Isolating and Analyzing Developing Endoderm", Cell Stem Cell, Mar. 4, 2011, vol. 8, pp. 335-346.
Written Opinion of the International Searching Authority issued in PCT/JP2015/084379 (PCT/ISA/237), dated Mar. 15, 2016.
English translation of International Preliminary Report on Patentability and Written Opinion dated Jun. 22, 2017, in PCT International Application No. PCT/JP2015/084379.

* cited by examiner

Induction/Amplification/Differentiation Methods for Human iPS Cell-Derived Primitive Gut Endoderm Cells (PGECs)

Effect of Rock Inhibitor Addition at the Time of Passaging of DE

Review of Method for Inducing Human iPS Cell-Derived PGECs

Review of Method for Amplifying Human iPS Cell-Derived PGECs

Morphology of Human iPS Cell-Derived PGECs after Amplification

Morphology of Human iPS Cell-Derived PGECs after Cryopreservation/Thawing

Growth Curve of Human iPS Cell-Derived PGECs

FACS Time Lapse Analysis of Human iPS Cell-Derived PGECs

Immunological Analysis of Human iPS Cell-Derived PGECs

Immunological Analysis of Human iPS Cell-Derived PGECs

Principal Component Analysis of Human iPS Cell-Derived PGECs

Hierarchical Clustering of Human iPS Cell-Derived PGECs

It is suggested that samples at P1 and thereafter are located at a ifferentiation stage between DE and HE.

It is suggested that samples at P0 are located at a differentiation stage corresponding to DE (EP).

Stepwise Induction of Hepatocytes Using iPSC-PGEC

Functional Analysis of iPSC-PGEC-Derived Hepatocytes

Hepatocyte Induction Capacity of Passaged iPSC-PGEC

Hepatocyte Induction Capacity of Passaged iPSC-PGEC

Directed Differentiation into Pancreatic Cells

Directed Differentiation of PGEC into Pancreatic Cells

Insulin: beta cells
Somatostatin: δ-cells or D cells
Glucagon: alpha cells of the pancreas
Amylase: pancreatic acinar cells
CD24-positive cells could differentiate into insulin-producing cells P16

Induction of Intestinal Tissues Using PGEC

Intestinal Tissues Induced from PGEC

Extraction of Positive/Negative Marker Genes Specific to PGEC (P1 and thereafter)

Reproducible generation of primitive gut endoderm cells from different patient-derived iPSC lines Generating multiple tissues of endodermal origin from transplanted PGEC In vitro generation and differentiation of liver bud into mature hepatic tissues grown from PGEC

PRIMITIVE GUT ENDODERM CELLS AND METHOD FOR PRODUCING SAME

TECHNICAL FIELD

The present invention relates to primitive gut endoderm cells and a method for producing the same. More specifically, the present invention relates to endoderm cells capable of differentiating into hepatocytes, pancreatic cells and intestinal cells, as well as a method for producing such endoderm cells.

BACKGROUND ART

Recently, realization of drug discovery screening to develop new medicines or regenerative medicine to complement the lost function of organs, both using tissues/organs induced from pluripotent stem cells such as iPS or ES cells, has attracted attention (Takebe, et al., Nature, 499: 481-484, 2013 (Non-Patent Document No. 1); WO2013/047639 A1: Method for producing tissue and organ (Patent Document No. 1)).

In order to realize regenerative medicine for liver diseases using human iPS cells, a technique for producing "a vast quantity" of human hepatocytes of GMP grade is required. For example, in order to enable about 30% function replacement of human adult liver, it is essential to transplant and engraft $6\times10^{10}$ hepatocytes per patient. Speaking of the production of this vast quantity of human hepatocytes, a cost estimate by the present inventors has revealed that when an attempt is made to prepare cells by a differentiation inducing protocol according to an existing prior art technology, a treatment of one patient on a waiting list for liver transplantation requires a huge cost amounting to approximately 9.5 billion yen if transplantation efficiency is taken into account.

PRIOR ART LITERATURE

Non-Patent Documents

Non-Patent Document No. 1: Takebe, et al., Nature, 499: 481-484, 2013

Patent Documents

Patent Document No. 1: WO2013/047639 A1

DISCLOSURE OF THE INVENTION

Problem for Solution by the Invention

Since most of the costs for regenerative medicine for liver diseases are spent by differentiation-inducing factors such as cytokines needed for differentiation and induction from human iPS cells, establishing "primitive gut endoderm cells (PGECs)" as a very important intermediate stage in the differentiation process from human iPS cells to organ cells is believed to be an extremely advantageous strategy for achieving huge cost reduction. Briefly, by establishing PGECs, the time period required for differentiation and induction is largely reduced and scattering among individual directed differentiations is minimized; for these and other advantages, this strategy provides a technological platform for inducing human organ cells at a low cost, stably and yet in a large quantity.

With a view to overcoming such technical obstacles, three approaches have been attempted recently. (1) Endoderm progenitor cells induced from iPS cells (Cell Stem Cell. 2012 Apr. 6; 10(4): 371-84; WO 2012178215 A1), (2) Foregut endoderm cells (Stem Cell Report, Vol. 1, 293-306, 2013) and (3) Pluripotent endoderm cells obtained by direct reprograming (Nature 508, 93-97, 2014). Briefly, cells of intermediate stages prepared by the above methods (1) to (3), respectively, are amplified and used for differentiation and induction into functional cells. However, method (1) is difficult to apply clinically because mouse cells are used as feeder cells. In method (2), the differentiation function of cells induced from the amplified cells is remarkably low. In method (3), the cells to be amplified have a safety problem, i.e., expression of markers such as CXCR4 that are associated with cancer malignancy such as metastasis is observed. For these and other problems, it has been difficult to date to apply each of these cells to medical or industrial purposes.

It is an object of the present invention to solve these problems of the prior art.

Means to Solve the Problem

As a result of intensive and extensive researches, the present inventors have established the induction of "primitive gut endoderm cells (PGECs)" positioned at an intermediate stage between the cells of (1), (3) above and the cells of (2) above. Further, after amplification of the resultant cells, the present inventors have also succeeded in differentiation and induction into functional cells. The primitive gut endoderm cells (PGECs) of the present invention are superior to the above-described cells of (1), (2) and (3). Briefly, the PGECs of the present invention are capable of differentiating into hepatocytes, pancreatic cells and intestinal cells (high in differentiation function) (superior to the cells of (2) above), do not express such markers as CXCR4 that are associated with cancer malignancy (high in safety) (superior to the cells of (3) above), and are easily applicable to clinical purposes since they can be prepared without feeder cells (superior to the cells of (1) above).

A summary of the present invention is as described below.

(1) A cell inducible after differentiating pluripotent stem cells and then passaging the resultant cells at least once or more times, which is negative for undifferentiated (pluripotent) cell markers NANOG, OCT4, MYC and LIN28A, negative for endoderm cell markers CXCR4, CERT, HHEX and GATA4, positive for intestinal endoderm cell markers CDX2 and HOXB9, negative for a mesenchymal cell marker brachyury (T), negative for a pancreatic cell marker PDX1, and capable of differentiating into at least a hepatocyte, a pancreatic cell and an intestinal cell.

(2) A method of preparing the cells of (1) above, comprising culturing pluripotent stem cells without feeder cells in the presence of Rock Inhibitor at the first stage, in the presence of Activin A and Wnt3a at the second stage, in the presence of BMP4, bFGF, VEGF and Activin A at the third stage and in the presence of BMP4, bFGF, VEGF and Activin A at the fourth stage, to thereby effect differentiation and then passaging the resultant cells at least once or more times.

(3) A method of amplifying the cells of (1) above, comprising culturing the cells in the presence of Rock Inhibitor at the first stage after passage or on the first day of passage and thereafter in the presence of SFD, FGF2, VEGF, EGF, A83-01 and Chir99021.

(4) A method of preparing organ cells, comprising differentiation and induction of the cells of (1) above into organ cells.

(5) A method of constructing a working cell bank for preparing organ cells, comprising cryopreserving the cells of (1) above at an arbitrary stage.

Effect of the Invention

According to the present invention, differentiation and induction of human iPS cells into PGECs which represent an intermediate stage of differentiation is possible without using feeder cells. These PGECs permit large scale production and using these cells, organ buds (Takebe, et al. Nature, 499: 481-484, 2013) can be prepared.

It was possible to amplify the induced PGECs $10^{10}$ times by passaging the cells 20 times or more, even in the absence of feeder cells which were essential in conventional methods. Further, the thus amplified cells could be stocked by cryopreservation.

Further, the PGECs having a capacity for differentiating into various functional cells such as hepatocytes, pancreatic cells and intestinal cells could be differentiated and induced into highly functional cells even after repeating passages which were a problem in conventional methods.

The present invention encompasses the contents disclosed in the specification and/or drawings of Japanese Patent Application No. 2014-248694 based on which the present patent application claims priority.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 15-1 shows morphological changes of hepatocytes differentiated and induced stepwise from amplified human iPS cell-derived PGECs (P6) (upper panel) and the results of gene expression analyses of hepatocyte differentiation markers (lower panel).

FIG. 15-2 shows a low magnification image of hepatocytes differentiated and induced from amplified human iPS-derived PGECs (P6); mature hepatocytes exhibiting a uniform morphology over a wide area have been induced.

FIG. 17-1 shows morphological observations of hepatocytes (PGEC-MH) after passages (P2, 4, 6, 9) which were differentiated and induced from human iPS cell-derived PGECs.

FIG. 17-2 shows the results of microarray analyses of hepatocytes (PGEC-MH) after passages (P3, 5) which were differentiated and induced from human iPS cell-derived PGECs (left panel) and the ALB secretion abilities of the same hepatocytes (PGEC-MH) before passage (P0) and after passages (P5, 10).

B: Albumin secretion ability of PGEC-derived liver buds. Human albumin was detected from the stage at day 4 of differentiation and induction using HCM/ECM. When compared to tissues from a sphere culture of PGEC alone (i.e., tissues obtained by harvesting PGECs alone, plating at a density of $5\times10^5$ cells/well/24-well plate in low-adhesive culture plates with a shape in which cells gather at the bottom, and culturing for several days), PGEC-derived liver buds showed a significantly high albumin secretion ability. When KO-DMEM/EGM mixed medium was used instead of HCM/EGM mixed medium, albumin secretion was not confirmed.

Figure 27:
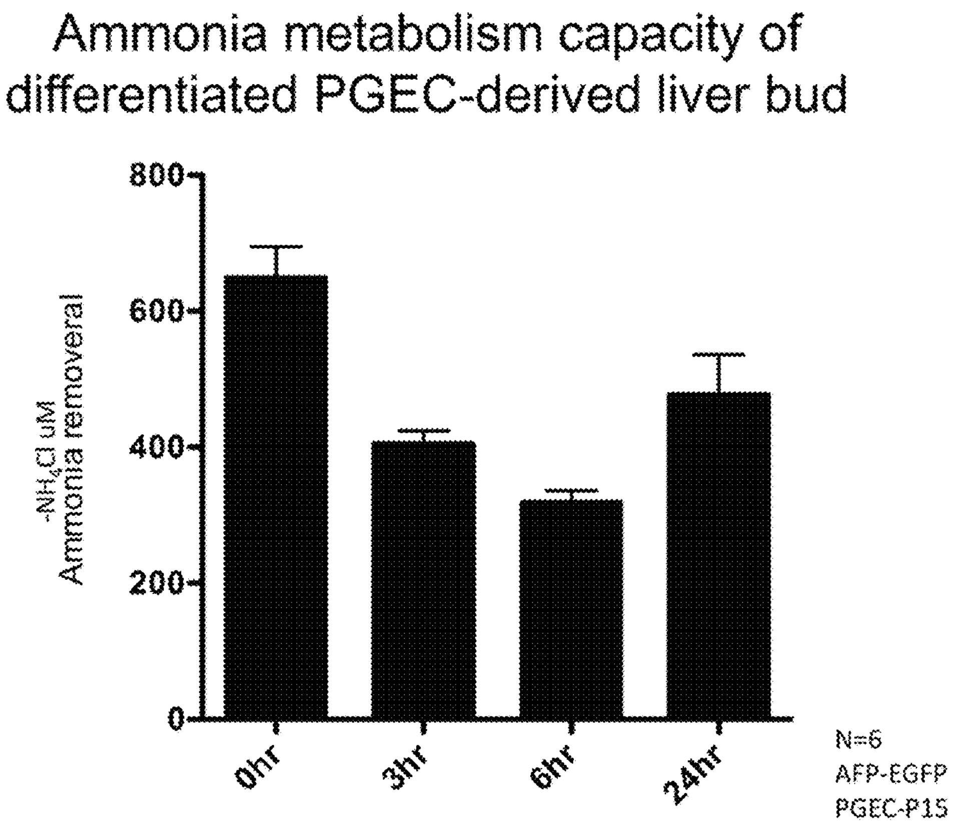

FIG. 27 illustrates ammonia metabolizing function of differentiated and induced PGEC-derived liver buds; the differentiated and induced PGEC-derived liver buds had a remarkable ammonia metabolizing function.

Figure 28:
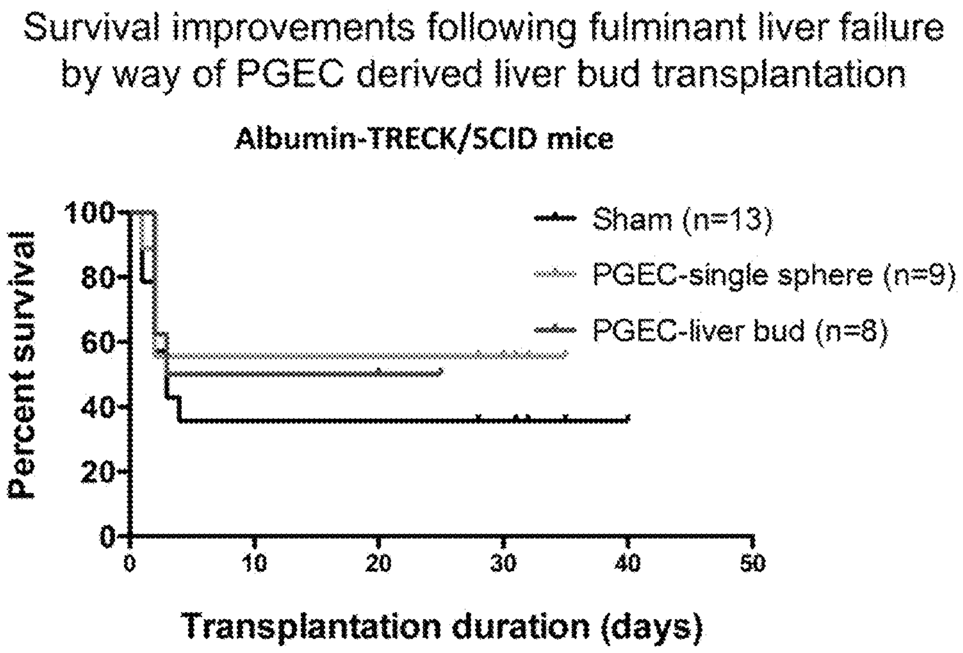

FIG. 28 illustrates therapeutic effect of PGEC-derived liver bud transplantation into fulminant liver failure model. Survival ratios were improved in PGEC-derived sphere- or liver bud-transplanted groups, as compared to non-transplanted groups.

Figure 29:
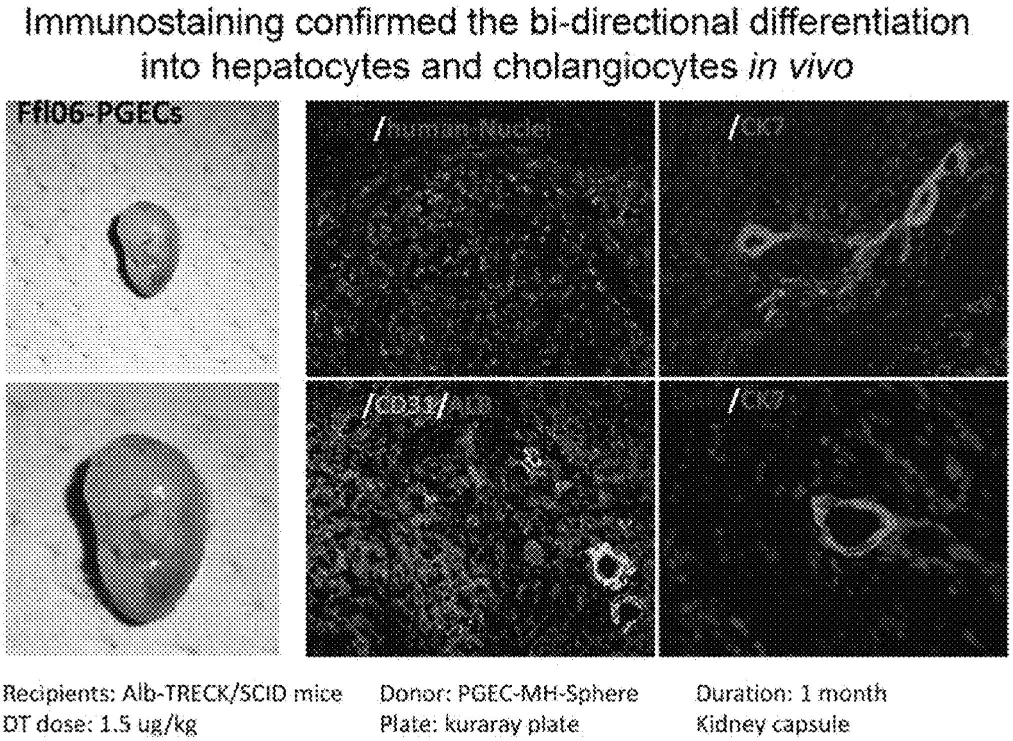

FIG. 29 confirms differentiation and induction into hepatocytes and bile duct epithelial cells by immunohistochemical staining. A: PGEC-derived liver bud-transplanted tissues forming at one month from the transplantation were vascularized tissues. No findings were observed in which teratoma or malignant tumor was suspected. B: The results of immunohistochemical staining revealed that liver tissues showing stainability for human nucleus specific antigen, human albumin (hepatocytes), human CK7 (bile duct epithelial cells) and human CD31 (blood vessels) had been formed. Scale bar=50 μm.

BEST MODES FOR CARRYING OUT THE INVENTION

Hereinbelow, the present invention will be described in more detail.

The present invention provides cells inducible after differentiating pluripotent stem cells and then passaging the resultant cells at least once or more times, which are negative for undifferentiated (pluripotent) cell markers NANOG, OCT4, MYC and LIN28A, negative for endoderm cell markers CXCR4, CER1, HHEX and GATA4, positive for intestinal endoderm cell markers CDX2 and HOXB9, negative for a mesenchymal cell marker brachyury (T), negative for a pancreatic cell marker PDX1, and capable of differentiating into at least hepatocytes, pancreatic cells and intestinal cells (hereinafter, the cells are sometimes referred to as primitive gut endoderm cells, PGE or PGECs in the present specification).

The cells of the present invention (PGECs) are induced after differentiating pluripotent stem cells and then passaging the resultant cells at least once or more times. As used herein, the tend "pluripotent stem cell" refers to a cell that latently has a capacity to differentiate into various tissues of the body (differentiation versatility). Specifically, pluripotent stem cell refers to a cell that is capable of differentiating into any of endodemi, mesoderm and ectoderm. Specific examples of pluripotent stem cell include, but are not limited to, induced pluripotent stem (iPS) cells and embryonic stem (ES) cells. The pluripotent stem cells used in the present invention may be human derived cells. Pluripotent stem cells derived from animals such as mouse, rat, dog, pig, monkey, sheep, cattle or chicken may also be used.

For differentiation of pluripotent stem cells, pluripotent stem cells may be cultured without feeder cells in the presence of Rock Inhibitor at the first stage, in the presence of Activin A and Wnt3a at the second stage, in the presence of BMP4, bFGF, VEGF and Activin A at the third stage and in the presence of BMP4, bFGF, VEGF and Activin A at the fourth stage, to thereby effect differentiation and then passaging the resultant cells at least once or more times. For example, when the initial day of culture is designated as Day 0, pluripotent stem cells may be cultured without feeder cells in the presence of Rock Inhibitor on Day 0, in the presence of Activin A and Wnt3a on Day 1, in the presence of BMP4, bFGF, VEGF and Activin A from Day 2 to Day 3 and in the presence of BMP4, bFGF, VEGF and Activin A from Day 4 to Day 5. However, the method of differentiation is not limited to this exemplary method. With respect to medium, SDF medium, RPMI medium, combinations thereof, and the like may be used.

Figure 10:
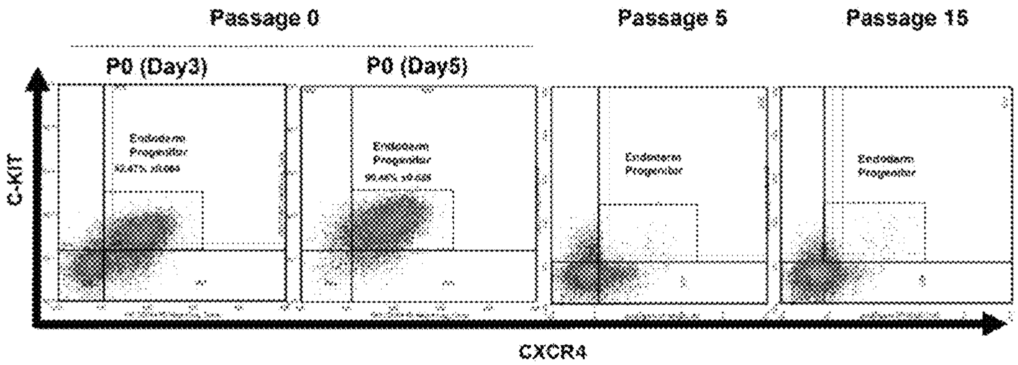
FIG. 10 shows the results of FACS time-lapse analyses of human iPS cell-derived PGECs before passage (P0) and after passages (P5, 15).

At least one or more passages are carried out. The number of times of passaging (passage number) is not particularly limited as long as the cells of the present invention (PGECs) can be obtained. Preferably, passage number is 1 to 30; more preferably, 1 to 20. After differentiation of pluripotent stem cells, passage may be started when confluency (the percentage of culture vessel occupied by cells) has reached about 80-90%. In such a state, a cell population is generated which, upon FACS analysis, is almost (80% or more) positive for antigens c-kit and CXCR4 as shown in FIG. 10. The present inventors, however, employ a method in which all cells (including those negative for c-kit and CXCR4) are passaged together (the process is simple and convenient), and the absence of the need for separation may well be described another advantage of this method.

Passage(s) may be carried out in SFD medium supplemented with A83-01, CHIR, VEGF, EGF and FGF2. However, medium for passage is not limited to this medium.

It was observed that a group of HOX genes such as CDX2 and HOXB9 are induced after passage(s).

Cell culture may be carried out in culture incubators at 37° C., 5% $CO_2$. In one embodiment of the present invention, for example, pluripotent stem cells ($2-6\times10^5$ cells) are seeded in SFD medium (1.5-2 ml, preferably 2 ml) supplemented with Rock Inhibitor (1-20 μM, preferably 10 μM) (Day 0). After one-day culture, the medium is exchanged with SFD medium (1.5-4 ml, preferably 2 ml) supplemented with Wnt3a (1-100 ng/ml, preferably 50 ng/ml) and Activin A (50-150 ng/ml, preferably 100 ng/ml) (Day 1), followed by another one-day culture. Subsequently, SFD medium and RPMI1640 medium are mixed at a ratio of 1:1 to 1:10 (preferably 1:9). To the resultant medium, BMP4 (0.5-4 ng/ml, preferably 2 ng/ml), bFGF (5-10 ng/ml, preferably 5 ng/ml), VEGF (5-50 ng/ml, preferably 10 ng/ml) and Activin A (50-150 ng/ml, preferably 100 ng/ml) are added. With the resultant medium, medium exchange is performed, followed by two-day culture (Day 2-Day 3). Thereafter, medium exchange is performed further with SFD medium (1.5-2 ml, preferably 2 ml) supplemented with BMP4 (0.5-5 ng/ml, preferably 2 ng/ml), bFGF (5-10 ng/ml, preferably 5 ng/ml), VEGF (8-20 ng/ml, preferably 10 ng/ml) and Activin A (50-150 ng/ml, preferably 100 ng/ml), followed by two-day culture (Day 4-Day 5). The thus cultured cells are designated as P0 cells (passage 0) and subjected to passaging. For example, P0 cells (500–$4\times10^5$ cells, preferably $1\times10^5$ cells) are seeded in PGE maintenance medium, followed by medium exchange once in every 3-4 days. The PGE maintenance medium is SFD medium (1.5-2 ml, preferably 2 ml) supplemented with FGF2 (5-10 ng/ml, preferably 5 ng/ml), VEGF (8-20 ng/ml, preferably 10 ng/ml), EGF (10-40 ng/ml, preferably 20 ng/ml), A83-01 (0.1-1 μM, preferably 0.5 μM) and Chir99021 (1-5 μM, preferably 3 μM).

In another embodiment of the present invention, for example, pluripotent stem cells (2–$6\times10^5$ cells) are seeded in B27 (2%)-added RPMI/1640 medium (1.5-2 ml, preferably 2 ml) supplemented with Rock Inhibitor (1-20 μM, preferably 10 μM) (Day 0). After one day culture, the medium is exchanged with B27 (2%)-added RPMI/1640 medium (1.5-4 ml, preferably 2 ml) supplemented with Wnt3a (1-100 ng/ml, preferably 50 ng/ml) and Activin A (50-150 ng/ml, preferably 100 ng/ml) (Day 1), followed by another one day culture. Subsequently, to B27 (2%)-added RPMI/1640 medium (1.5-4 ml, preferably 2 ml), BMP4 (0.5-4 ng/ml, preferably 2 ng/ml), bFGF (5-10 ng/ml, preferably 5 ng/ml), VEGF (5-50 ng/ml, preferably 10 ng/ml) and Activin A (50-150 ng/ml, preferably 100 ng/ml) are added. With the resultant medium, medium exchange is performed, followed by two-day culture (Day 2-Day 3). Thereafter, medium exchange is performed further with SFD medium (1.5-2 ml, preferably 2 ml) supplemented with BMP4 (0.5-5 ng/ml, preferably 2 ng/ml), bFGF (5-10 ng/ml, preferably 5 ng/ml), VEGF (8-20 ng/ml, preferably 10 ng/ml) and Activin A (50-150 ng/ml, preferably 100 ng/ml), followed by two-day culture (Day 4-Day 5 or Day 4). The thus cultured cells are designated as P0 cells (passage 0) and subjected to passaging. For example, P0 cells (500–$4\times10^5$ cells, preferably $1\times10^5$ cells) are seeded in PGE maintenance medium, followed by medium exchange once in every 3-4 days. The PGE maintenance medium is SFD medium (1.5-2 ml, preferably 2 ml) supplemented with FGF2 (5-10 ng/ml, preferably 5 ng/ml), VEGF (8-20 ng/ml, preferably 10 ng/ml), EGF (10-40 ng/ml, preferably 20 ng/ml), A83-01 (0.1-1 μM, preferably 0.5 μM) and Chir99021 (1-5 μM, preferably 3 μM).

The cells of the present invention (PGECs) are negative for undifferentiated (pluripotent) cell markers NANOG, OCT4, MYC and LIN28A, negative for endoderm cell markers CXCR4, CER1, HHEX and GATA4, positive for intestinal endoderm cell markers CDX2 and HOXB9, negative for a mesenchymal cell marker brachyury (T), and negative for a pancreatic cell marker PDX1. Besides, it is preferable that the cells of the present invention (PGECs) are positive for intestinal endoderm cell markers HOXBS, HOXB6, HOXB7, HOXB8, HOXA9 and HOXC9, negative for a mesenchymal cell marker PDGFRA, and negative for a hepatocyte marker ALB.

The cells of the present invention (PGECs) are capable of differentiating into organ cells such as hepatocytes, pancreatic cells and intestinal cells. Differentiation and induction into hepatocytes, pancreatic cells or intestinal cells may be performed by the methods disclosed in the Examples described later. When the organ cell of interest is hepatocytes, differentiation and induction into hepatocytes may be achieved by culturing the PGECs of the present invention in the presence of, for example, FBS, HGF, OSM and DEX (see Examples described later). When the organ cell of interest is pancreatic cells, differentiation and induction into pancreatic cells may be achieved by culturing the PGECs of the present invention in the presence of, for example, L-glutamine, glucose, ascorbic acid, SB431542, 2-M insulin and nicotinamide (see Examples described later). When the organ cell of interest is intestinal cells, differentiation and induction into intestinal cells may be achieved by culturing the PGECs of the present invention in the presence of, for example, B27, R-Spondin1, Noggin and EGF (see Examples described later).

The cells of the present invention (PGECs) permit cryopreservation. The timing for cryopreservation is not particularly limited. Preferably, the cells are cryopreserved after 1-20 passages, more preferably after 2-10 passages.

It is an advantage of the cells of the present invention that common cell freezing/thawing procedures may be used. However, in particular, it is important that (a) the work involved until freezing the cells after they are mixed with preservation solvent and (b) the operation for thawing the frozen cells after preservation be carried out promptly.

Since the cells of the present invention (PGECs) can be cryopreserved, it is possible to use them as a working cell bank for preparing endoderm-derived cells, tissues or organs for use in clinical/drug discovery applications. Therefore, the present invention also provides a method of constructing a working cell bank for preparing organ cells, comprising cryopreserving the PGECs at an arbitrary stage.

For preparing the cells of the present invention (PGECs), pluripotent stem cells may be cultured without feeder cells in the presence of Rock Inhibitor at $1^{st}$ stage, in the presence of Activin A and Wnt3a at $2^{nd}$ stage, in the presence of BMP4, bFGF, VEGF and Activin A at $3^{rd}$ stage and in the presence of BMP4, bFGF, VEGF and Activin A at $4^{th}$ stage, to thereby effect differentiation and then passaged at least once or more times. For example, when the initial day of culture is designated as Day 0, pluripotent stem cells may be cultured without feeder cells in the presence of Rock Inhibitor on Day 0, in the presence of Activin A and Wnt3a on Day 1, in the presence of BMP4, bFGF, VEGF and Activin A from Day 2 to Day 3 and in the presence of BMP4, bFGF, VEGF and Activin A from Day 4 to Day 5, to thereby effect differentiation and then passaged at least once or more times. However, the method of preparation of the cells of the present invention (PGECs) is not limited to this method. With respect to medium, SFD medium, RPMI medium, combinations thereof, and the like may be used.

Passaging is as described above.

Cell culture may be carried out in culture incubators at 37° C., 5% $CO_2$.

In one embodiment of the present invention, for example, pluripotent stem cells (2–$6\times10^5$ cells) are seeded in SFD medium (1.5-2 ml, preferably 2 ml) supplemented with Rock Inhibitor (1-20 μM, preferably 10 μM) (Day 0). After one day culture, the medium is exchanged with SFD medium (1.5-4 ml, preferably 2 ml) supplemented with Wnt3a (1-100 ng/ml, preferably 50 ng/ml) and Activin A (50-150 ng/ml, preferably 100 ng/ml) (Day 1), followed by another one day culture. Subsequently, SFD medium and RPMI1640 medium are mixed at a ratio of 1:1 to 1:10

(preferably 1:9). To the resultant medium, BMP4 (0.5-4 ng/ml, preferably 2 ng/ml), bFGF (5-10 ng/ml, preferably 5 ng/ml), VEGF (5-50 ng/ml, preferably 10 ng/ml) and Activin A (50-150 ng/ml, preferably 100 ng/ml) are added. With the resultant medium, medium exchange is performed, followed by two-day culture (Day 2-Day 3). Thereafter, medium exchange is performed further with SFD medium (1.5-2 ml, preferably 2 ml) supplemented with BMP4 (0.5-5 ng/ml, preferably 2 ng/ml), bFGF (5-10 ng/ml, preferably 5 ng/ml), VEGF (8-20 ng/ml, preferably 10 ng/ml) and Activin A (50-150 ng/ml, preferably 100 ng/ml), followed by two-day culture (Day 4-Day 5). The thus cultured cells are designated as P0 cells (passage 0) and subjected to passaging. For example, P0 cells ($500-4\times10^5$ cells, preferably $1\times10^5$ cells) are seeded in PGE maintenance medium, followed by medium exchange once in every 3-4 days. The PGE maintenance medium is SFD medium (1.5-2 ml, preferably 2 ml) supplemented with FGF2 (5-10 ng/ml, preferably 5 ng/ml), VEGF (8-20 ng/ml, preferably 10 ng/ml), EGF (10-40 ng/ml, preferably 20 ng/ml), A83-01 (0.1-1 μM, preferably 0.5 μM) and Chir99021 (1-5 μM, preferably 3 μM).

In another embodiment of the present invention, for example, pluripotent stem cells ($2-6\times10^5$ cells) are seeded in B27 (2%)-added RPMU1640 medium (1.5-2 ml, preferably 2 ml) supplemented with Rock Inhibitor (1-20 preferably 10 μM) (Day 0). After one day culture, the medium is exchanged with B27 (2%)-added RPM/1640 medium (1.5-4 ml, preferably 2 ml) supplemented with Wnt3a (1-100 ng/ml, preferably 50 ng/ml) and Activin A (50-150 ng/ml, preferably 100 ng/ml) (Day 1), followed by another one day culture. Subsequently, to B27 (2%)-added RPMI/1640 medium (1.5-4 ml, preferably 2 ml), BMP4 (0.5-4 ng/ml, preferably 2 ng/ml), bFGF (5-10 ng/ml, preferably 5 ng/ml), VEGF (5-50 ng/ml, preferably 10 ng/ml) and Activin A (50-150 ng/ml, preferably 100 ng/ml) are added. With the resultant medium, medium exchange is performed, followed by two-day culture (Day 2-Day 3). Thereafter, medium exchange is performed further with SFD medium (1.5-2 ml, preferably 2 ml) supplemented with BMP4 (0.5-5 ng/ml, preferably 2 ng/ml), bFGF (5-10 ng/ml, preferably 5 ng/ml), VEGF (8-20 ng/ml, preferably 10 ng/ml) and Activin A (50-150 ng/ml, preferably 100 ng/ml), followed by two-day culture (Day 4-Day 5 or Day 4). The thus cultured cells are designated as P0 cells (passage 0) and subjected to passaging. For example, P0 cells ($500-4\times10^5$ cells, preferably $1\times10^5$ cells) are seeded in PGE maintenance medium, followed by medium exchange once in every 3-4 days. The PGE maintenance medium is SFD medium (1.5-2 ml, preferably 2 ml) supplemented with FGF2 (5-10 ng/ml, preferably 5 ng/ml), VEGF (8-20 ng/ml, preferably 10 ng/ml), EGF (10-40 ng/ml, preferably 20 ng/ml), A83-01 (0.1-1 μM, preferably 0.5 μM) and Chir99021 (1-5 μM, preferably 3 μM).

Further, for amplifying the cells of the present invention (PGECs), the cells may be cultured in the presence of Rock Inhibitor at the first stage after passage or on the first day of passage and thereafter in the presence of SFD, FGF2, VEGF, EGF, A83-01 and Chir99021. For example, when the initial day of culture after passage is designated as Day 0, PGECs may be amplified by culturing in the presence of Rock Inhibitor on Day 0 and thereafter in the presence of SFD, FGF2, VEGF, EGF, A83-01 and Chir99021. However, the method of amplification of the cells of the present invention (PGECs) is not limited to this method.

Cell culture may be carried out in culture incubators at 37° C., 5% $CO_2$.

In one embodiment of the present invention, for example, when the initial day of culture after passage or the first day of passage is designated as Day 0, PGECs ($500-4\times10^5$ cells, preferably $1\times10^5$ cells) are seeded in PGE maintenance medium supplemented with Rock Inhibitor (1-100 μM, preferably 10 μM) (Day 0) and on the following day, medium exchange with PGE maintenance medium is performed. Medium exchange is performed once in every 3-4 days. The PGE maintenance medium is SFD medium (1.5-2 ml, preferably 2 ml) supplemented with FGF2 (5-10 ng/ml, preferably 5 ng/ml), VEGF (8-20 ng/ml, preferably 10 ng/ml), EGF (10-40 ng/ml, preferably 20 ng/ml), A83-01 (0.1-1 μM, preferably 0.5 μM) and Chir99021 (1-5 μM, preferably 3 μM).

For preparation and/or amplification of the cells of the present invention (PGECs), the cells may be cultured on a support such as gel. As a preferable example of this support, 1:30 diluted Matrigel™ may be given, but other supports may also be used; e.g., laminin and derivatives thereof, vitronectin, agarose gel, acrylamide gel, hydrogel, collagen gel or urethane gel.

The present invention also provides a method of preparing organ cells (such as hepatocytes, pancreatic cells and intestinal cells) using the cells of the present invention (PGECs). Differentiation and induction into hepatocytes, pancreatic cells or intestinal cells may be performed by the methods disclosed in Examples described later. When the organ cell of interest is hepatocytes, differentiation and induction into hepatocytes may be achieved by culturing the PGECs of the present invention in the presence of, for example, FBS, HGF, OSM and DEX (see Examples described later). When the organ cell of interest is pancreatic cells, differentiation and induction into pancreatic cells may be achieved by culturing the PGECs of the present invention in the presence of, for example, L-glutamine, glucose, ascorbic acid, SB431542, 2-M insulin and nicotinamide (see Examples described later). When the organ cell of interest is intestinal cells, differentiation and induction into intestinal cells may be achieved by culturing the PGECs of the present invention in the presence of, for example, B27, R-Spondin1, Noggin and EGF (see Examples described later). The cells of the present invention (PGECs) are also capable of differentiating into organ cells other than hepatocytes, pancreatic cells and intestinal cells, e.g., pulmonary cells, thyroid cells, gastrointestinal secretory gland cells, peritoneal cells, pleural cells, pharyngeal cells, cells of eustachian tube/trachea/bronchus, and urinary tract cells. For differentiation and induction of organ cells from the cells of the present invention, the cells of the present invention may be cultured on a support such as gel. As a support, 1:30 diluted Matrigel™ is preferably used when planar differentiation and induction are attempted. When three-dimensional differentiation and induction by organ bud preparation is attempted, use of gel is preferable. Examples of such gel include, but are not limited to non-diluted to 1:4 diluted Matrigel™ agarose gel, acrylamide gel, hydrogel, collagen gel and urethane gel. Organ cells differentiated and induced from the cells of the present invention are highly functional. Furthermore, such organ cells are extremely high in homogeneity, compared to those organ cells differentiated and induced from conventional pluripotent stem cells (see Examples described later).

It is possible to prepare tissues or organs using organ cells prepared from the cells of the present invention (PGECs). For example, organ cells prepared from PGECs may be co-cultured with vascular endothelial cells and mesenchymal cells to produce organ buds, which are then transplanted into living bodies to thereby prepare tissues or organs (Takebe, et al., Nature, 499: 481-484, 2013 (Non-Patent Document No. 1); WO2013/047639 A1: Method for producing tissue and organ (Patent Document No. 1)).

EXAMPLES

Hereinbelow, the present invention will be described in details with reference to the following Examples.

[Example 1] Method for Amplifying PGECs Induced from iPS Cells

[Experimental Methods]

iPS cells (clones established independently from umbilical cord and TkDA3 clones kindly provided by Tokyo University) cultured on Matrigel™ coating were dissociated with Accutase and harvested. The cells were plated on Matrigel™-coated 6-well plates at a density of $2\text{–}6\times10^5$ cells/well using Rock Inhibitor (10 uM)-added SFD medium, followed by one day culture. Then, medium exchange was carried out with SFD medium supplemented with Wnt3a (50 ng/ml) and Activin A (100 ng/ml), followed by another one day culture. Subsequently, SFD medium and RPMI1640 medium were mixed at a ratio of 1:9, followed by addition of BMP4 (0.5 ng/ml), bFGF (5 g/ml), VEGF (10 ng/ml) and Activin A (100 ng/ml) thereto. Medium exchange was carried out with the resultant medium, followed by two-day culture. Thereafter, medium exchange was further carried out with SFD medium supplemented with BMP4 (0.5 ng/ml), bFGF (5 g/ml), VEGF (10 ng/ml) and Activin A (100 ng/ml), followed by two-day culture. The resultant cells were designated as PGE P0 and passaged in PGE maintenance medium.

PGE P0 cells were dissociated with Accutase and harvested. A ⅔ volume of the harvested cells were plated on Matrigel™-coated 6-well plates using PGE maintenance medium supplemented with Rock Inhibitor (10 μM). On the next day, the cells were harvested again, and the total volume of the cells were plated on 60 mm dishes using PGE maintenance medium supplemented with Rock Inhibitor (10 μM). On the next day, the cells were observed and when they were less than 80% confluent, medium exchange was carried out with PGE maintenance medium; when the cells were 80% confluent or more, passaging was carried out. Preferably, passaging is carried out at a ratio of 1/3-1/2 up to P5. When proliferation is rapid, a lower ratio may be employed. For passaging, cells were plated on Matrigel™-coated dishes using PGE maintenance medium supplemented with Rock Inhibitor (10 nM); on the next day, medium exchange was carried out with PGE medium. Medium exchange was carried out once in every 3-4 days. When the cells were plated on 100 mm dishes at a density of $3\times10^5$ cells/well, the cells reached confluence in 3 to 4 days. It should be noted that the timing of passaging is optimized by observing the state of the cells that are about to be passaged.

*For information, reagents used in the above-described differentiation and induction into PGE and into hepatocytes are summarized in the following Tables 1 to 3.

TABLE 1

List of Reagents Used in Differentiation and Induction into PGE and into Hepatocytes

| Common Name/ Abbreviation | Product Name | Manufacturer | Catalogue No. |
|---|---|---|---|
| Matrigel | Matrigel ™ growth factor reduced | Life Technologies | CC-354230 |
| RPMI | RPMI-1640 (Phenol Red) | Wako Pure Chemical | WK18902025 |
| mTeSR | mTeSR1 | Veritas | ST-05850 |
| IMDM | IMDM | Life Technologies | 12440-053 |
| F12 | F-12K Nutrient Mixture (Ham's F-12K) Kaighn's Modified | Life Technologies | 21127-022 |
| KO-DMEM | Knock-Out D-MEM | Life Technologies | 10829-018 |
| HCM | Hepatocyte Culture Media BulletKit (HCM BulletKit) | Lonza | LZ-CC-3198 |
| Acctase | Accurase | ICT | FN-AT104-500 |
| PBS | Phosphate buffer powder | Wako Pure Chemical | WK16714491 |
| B27 | B27 Additive (x50) | Life Technologies | 17504-044 |
| RockInhibitor | Y-27632 | wako | WK25100514 |
| ActivinA | Recombinant Human Activin A | R&D (Cosmo Bio) | 338-AC-01M |
| Wnt3a | Wnt-3a, Human, Recombinant | R&D (Cosmo Bio) | RSD-5036-WN-500-500 |
| BMP4 | BMP-4, human recombinant | Funakoshi | FN-314-BP |
| bFGF | bFGF, recombinant, human | WAKO | 060-04543 |
| VEGF | Vascular Endothelial Cell Growth Factor | Life technologies | PHC9391 |
| MTG | StemSyre 50 mmol/l Monothioglycerol | WAKO | WK19515791 |
| N2 | N2 Additive (x50) | Life Technologies | 17502-048 |
| ASP | Ascorbic Acid | SIGMA | A2343-500G |
| A83-01 | A-83-01 (TOC2939/10) | wako | WK51775771 |
| CHIR | CHIR99021 | CAY | FN-13122 |
| EGF | Epidermal Growth Factor | SIGMA | E9644-.5MG |
| DM3189 | LDN193189 hydrochloride | Wako Pure Chemical | 124-06011 |
| IWP2 | IWP2 | R&D | FN-3533/10 |
| PD0325901 | PD0325901 | TOCRIS | 4192/10 |
| RA | Retinoic Acid | wako | 182-01111 |
| KSR | KnockOut Serum Replacement | Life Technologies | 10828-028 |
| FBS | CELLect GOLD | MP Bio | 2916754 |
| NEAA | MEM NEAA (100x) | Life Technologies | 11140-050 |
| L-Glutamine | L-Glutemine 200 mM (100x) | Life Technologies | 25050-081 |
| 2-ME | 2-Mercaptoethanol | Life Technologies | 21985-023 |
| DMSO | Dimethyl Sulfoxide | Nacalai | KK-13445-74 |
| HGF | Recombinant human HGF | Kringle Pharma | |

TABLE 1-continued

| List of Reagents Used in Differentiation and Induction into PGE and into Hepatocytes | | | |
|---|---|---|---|
| Common Name/ Abbreviation | Product Name | Manufacturer | Catalogue No. |
| DEX | Dexamethasone-Water Soluble | SIGMA | QJ-D2915-100MG |
| OSM | Oncostatin M (OSM), human recombinant | RSD | FN-295-OSM-050 |

2. Preparation of Media Necessary for Differentiation and Induction into PGE and Maintenance Thereof Basal medium necessary for differentiation and induction into PGE and for PGE maintenance (hereinafter, called "SFD medium") and PGE maintenance medium are prepared. Tables 2 and 3 below show the compositions of SFD medium and PGE maintenance medium, respectively.

TABLE 2

| SFD Medium | |
|---|---|
| Reagent | Volume |
| IMDM | 500 mL |
| F12 | 160 mL |
| MTG | 6.6 mL |
| N2 | 3.3 mL |
| B27 | 3.3 mL |
| ASP | 660 μL |

TABLE 3

| PGE Maintenance Medium PGE maintenance medium is prepared by adding the following factors to SFD medium | |
|---|---|
| Reagent | Final Concentration |
| A83-01 | 0.5 μM |
| CHIR | 3 μM |
| VEGF | 10 ng/mL |
| EGF | 20 ng/mL |
| FGF2 | 5 ng/mL |

3. Matrigel™ Coating

Matrigel™ growth factor reduced was diluted to 1/30 with RPMI. The thus diluted solution was added to culture dishes in the necessary amount as indicated in Table 4 below, and spread over the whole surface. The dishes were left to stand at room temperature for about 2 hours. The diluted solution was recovered into a tube, and RPMI was added to the dishes in the same amount as the diluted solution. (Hereinafter, this coating operation is called "Matrigel™ coating".) The diluted solution could be used up to three times. Matrigel™ coating was performed before cell plating.

TABLE 4

| Necessary Amount of Diluted Solution | |
|---|---|
| Culture Dish | Amount of Diluted Solution |
| 6wellplate | 2 mL |
| 60 mm dish | 2 mL |
| 100 mm dish | 5 mL |

4. Cryopreservation and Thawing of PGEC Cells

Cryopreservation

When PGECs reached 90% confluence (about 3-4×$10^6$ cells per 100 mm dish), the cells were washed with 3 ml of sterile $Ca^+/Mg^+$-free PBS per 100 mm dish. Then, 1.5 ml of Accutase was added to the cells, followed by treatment in a 37° C., 5% $CO_2$ incubator for 2-5 min. Immediately thereafter, the cells were neutralized with 9 ml of DMEM-F12 and collected into 50 ml conical tubes. After cell counting, centrifugation was carried out (80-90 g, 5 min). The supernatant was discarded. Then, the cells were suspended gently in cell banker-1 which had been prepared to give a volume of 1 ml per 5×$10^5$ cells. The resultant cell suspension was transferred in 1-ml aliquots into cryopreservation tubes. The tubes were placed in an isopropanol-filled container for freezing at 1° C. (make sure that the lid was shut tightly); the container was then left to stand still in a freezer at −80° C. for one day. On the next day, the container was transferred into a liquid nitrogen tank and stored therein. According to this method, a long term preservation is possible, probably for two years or more.

Thawing

Frozen tubes containing PGECs were taken out of the liquid nitrogen tank, followed by rapid thawing in a water bath preset at 37° C. Immediately before complete thawing of the frozen cells (within less than 1 min), the tubes were taken out of the water bath and their periphery was immediately wiped with 70% ethanol in a safety cabinet; thereafter, the cells were transferred into a conical tube for centrifugation together with 9 ml of pre-warmed DMEM-F12. The cells were washed and centrifuged at 80-90 g for 5 min to give a pellet that was suspended in 10 μM Rock Inhibitor-added PGE maintenance medium which had been prepared to give a volume of 1 ml per 2×$10^4$ cells. The cell suspension was plated on Matrigel™ (growth factor reduced) (1:30 dilution)-coated 100 mm dish to give a total volume of 10 ml (=2×$10^5$ cells/100 mm dish). The cells were cultured in 37° C., 5% $CO_2$ incubator. From the following day, the cells were cultured in PGE maintenance medium (Rock Inhibitor free) with medium exchange being conducted very two days to effect amplification.

[Experimental Results]

Figure 1:
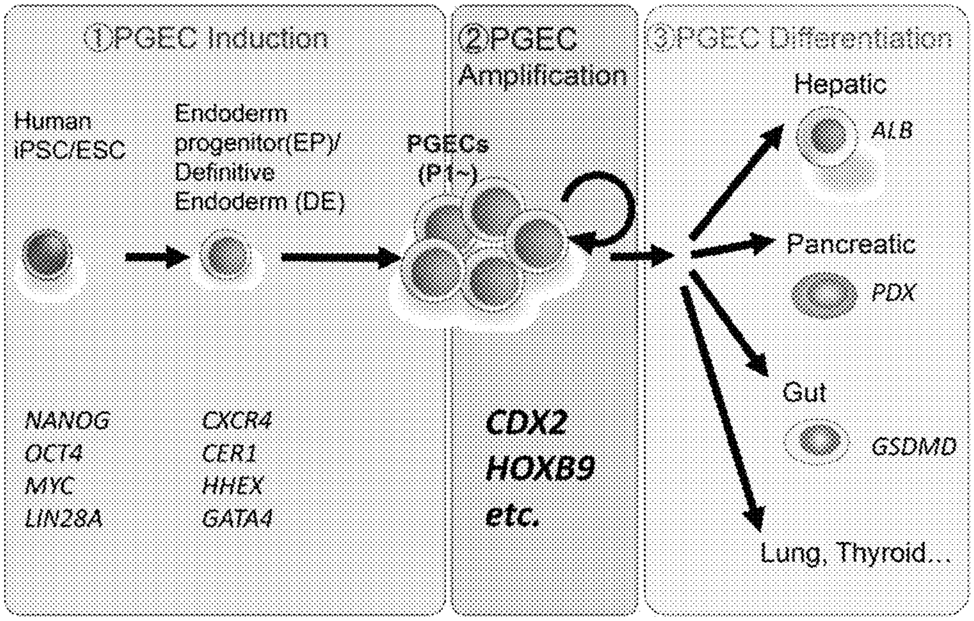
FIG. 1 shows an outline of induction/amplification/differentiation methods for human iPS cell-derived primitive gut endoderm cells (PGECs). The cells to be amplified by the present invention are primitive gut endoderm cells (PGECs) which are more differentiated (toward gut tube lineage) than, or located downstream of, those cells called definitive endoderm or endodermal progenitors. These PGECs are capable of differentiating into every cell derived from endoderm. Below or at the right of the designations of cells (Human iPSC/ESC, Endoderm progenitor (EP)/Definitive Endoderm (DE), PGECs), types of markers expressed by the relevant cells are indicated.

(1) An outline of this Example is shown in FIG. 1. Cells amplified by the present invention are primitive gut endoderm cells (PGECs) which are more differentiated (toward gut tube lineage) than, or located downstream of, those cells called definitive endoderm (D'Amour, K. A. et al. Efficient differentiation of human embryonic stem cells to definitive endoderm. Nature biotechnology 23, 1534-1541 (2005), Iwashita, H. et al. Secreted Cerberusl as a Marker for Quantification of Definitive Endoderm Differentiation of the Pluripotent Stem Cells. PloS one 8, e64291 (2013), Si-Tayeb, K. et al. Highly efficient generation of human hepatocyte-like cells from induced pluripotent stem cells. Hepatology 51, 297-305 (2010) and endodermal progenitor (Cheng, X. et al. Self-renewing endodermal progenitor lines generated from human pluripotent stem cells. Cell stem cell 10, 371-384 (2012)) cells. The PGECs are capable of differentiating into every cell derived from endoderm.

Figure 2:
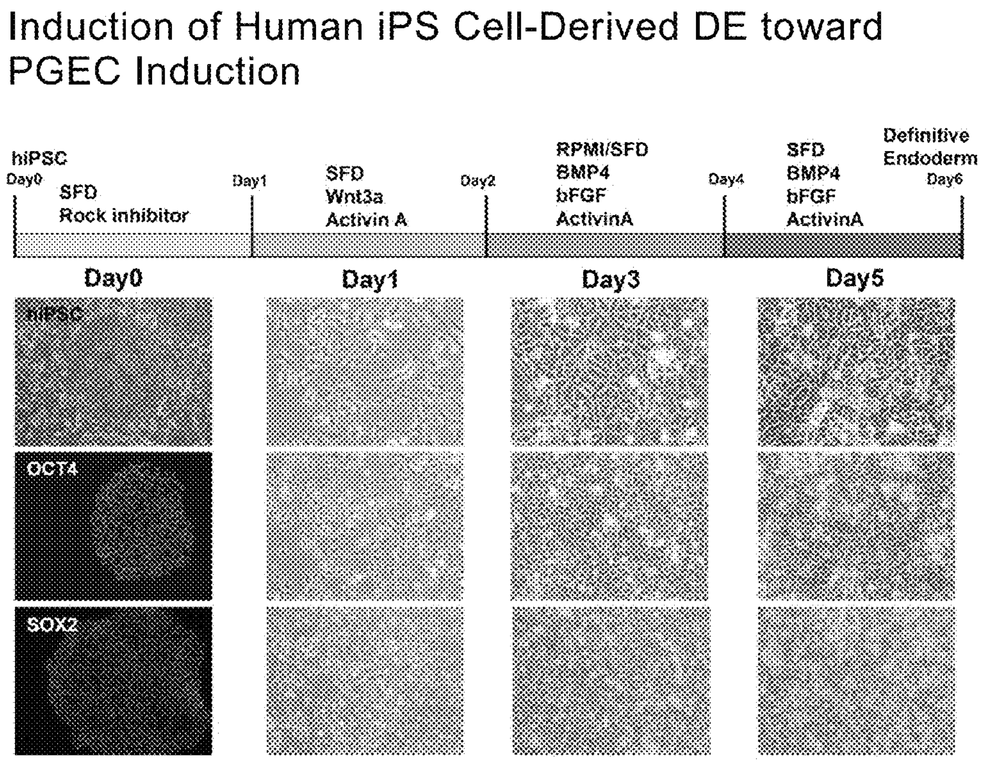
FIG. 2 shows early differentiation/induction process from human iPS cells to PGECs without passage, and morphological observation of cells.

(2) Morphological observation of cells in early differentiation and induction process from human iPS cells to PGECs without passage (FIG. 2). It was confirmed by colony morphology and immunostaining with OCT4 and SOX2 that undifferentiated property (pluripotency) of human iPS cells was sufficiently retained (Day 0). Subsequently, iPS cells of undifferentiated state were exposed to Activin A and cited differentiation factors successively to effect induction into definitive endoderm. By Day 6, a large number of cells were induced into pebble stone-like definitive endoderm cells with enlarged nuclei.

Figure 3:
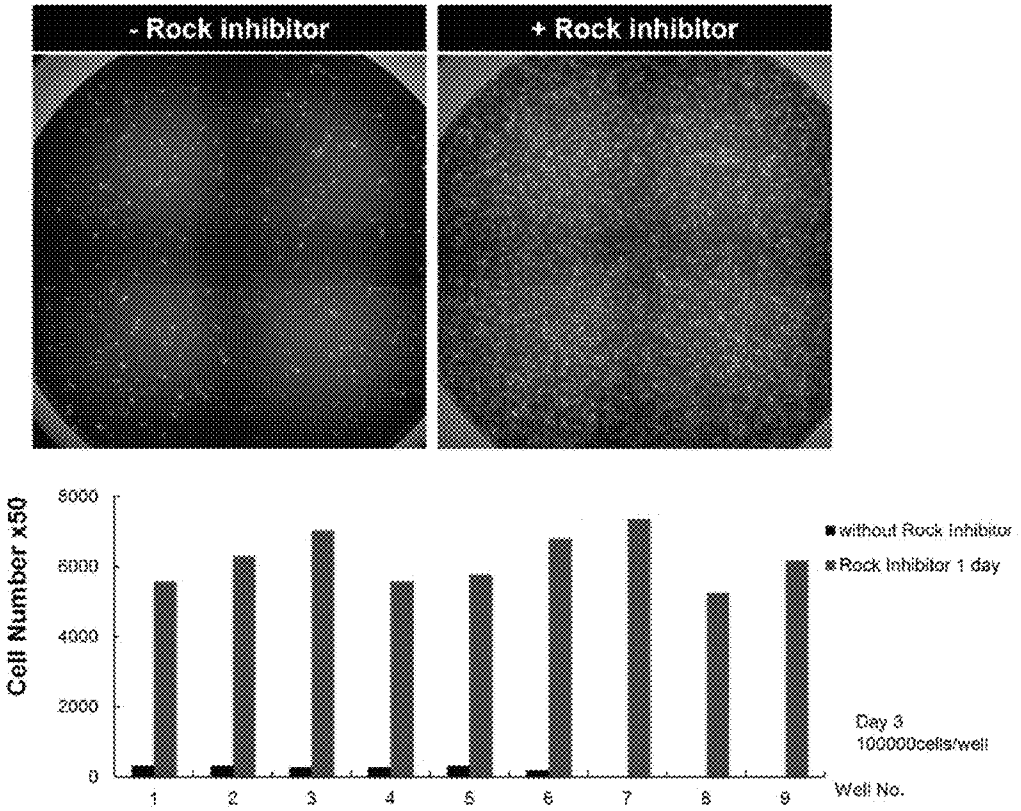
FIG. 3 shows that addition of Rock inhibitor caused great improvement in the adhesion and engraftment of passaged cells.

(3) A review of the utility of Rock Inhibitor immediately after passaging of PGECs (FIG. 3). Fluorescence-labeled PGECs were passaged, and the whole image of the culture dish at Day 3 was photographed (FIG. 3, upper panel). Briefly, PGECs induced from AAVS1::EGFP-iPS cells (TkDA) were passaged, followed by evaluation of survival/adhesion/proliferation with fluorescence of EGFP. Addition of Rock Inhibitor on the first day of plating enhanced the survival and adhesion of cells. On the other hand, in the absence of Rock Inhibitor, a large number of cells were unable to survive (FIG. 3, upper panel). The results of cell counting on the third day after plating revealed that the cell numbers in Rock Inhibitor exposure groups were remarkably large, suggesting enhanced cell proliferation (FIG. 3, lower panel). Horizontal axis represents data for each well (n).

Figure 4:
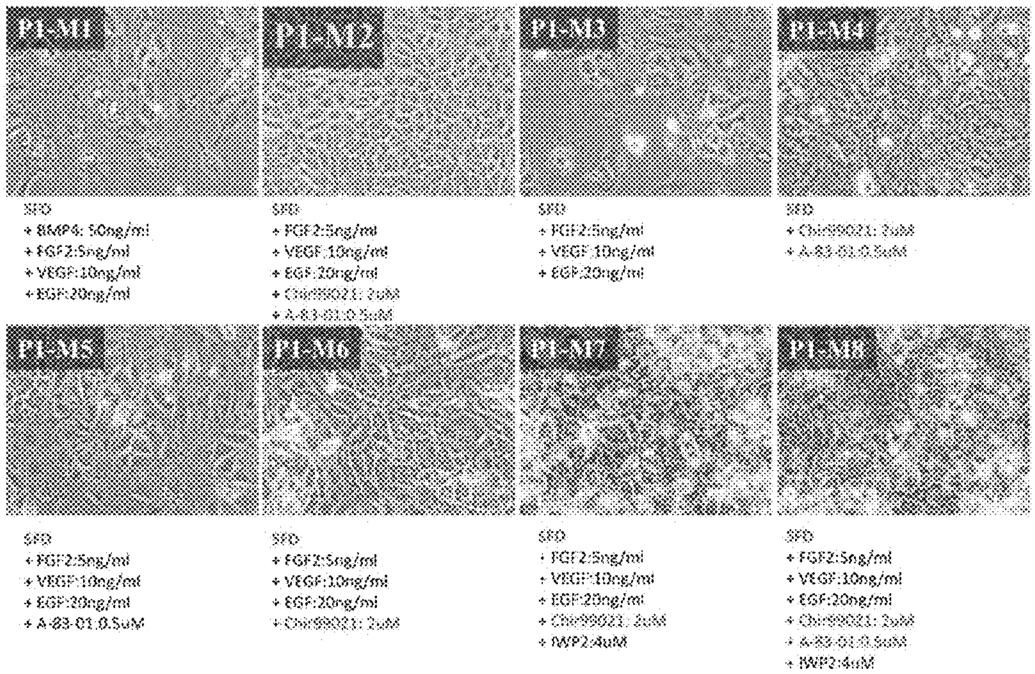
FIG. 4 reviews combinations of cytokines and additives effective for maintenance and amplification of PGECs after passage. Together with the results shown in FIG. 5, this Figure shows that the condition of M2 is effective.
Figure 5:
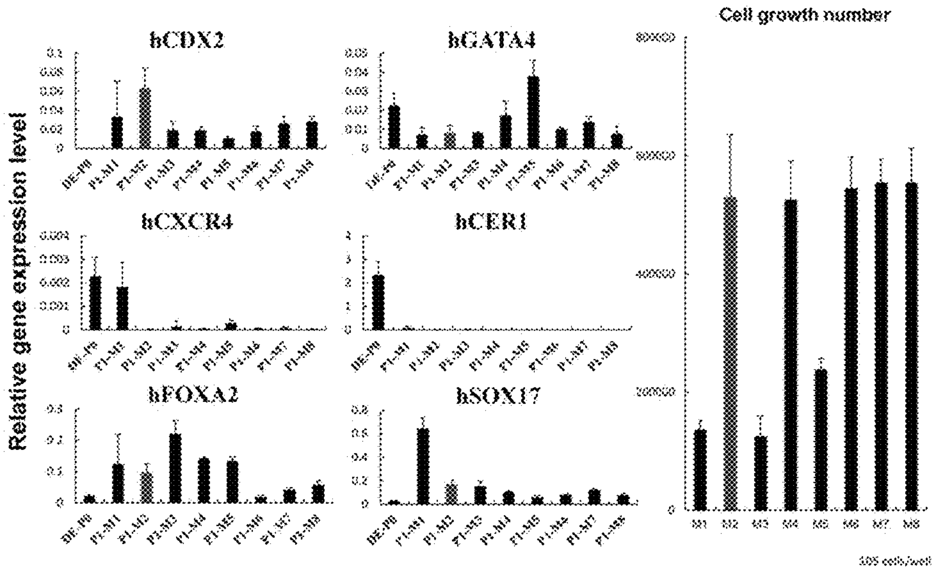
FIG. 5 shows comparison of gene expression levels in M1-8 in the left panel and the results of quantitative determination of cell growth number in the right panel. Among the conditions of M2, M4 and M6-8 allowing for good cell growth, M2 was shown to be a condition for enhancing the expression of a PGEC marker CDX2 while decreasing the expression of CXCR4 and CER1.

(4) A review of humoral factors useful for PGEC amplification after passaging (FIGS. 4 and 5). Induced definitive endoderm cells were cultured under such medium conditions that different cytokines and low molecular weight compounds were combined, to thereby search for optimum conditions. Cell morphologies obtained on the third day are shown in FIG. 4; the results of gene expression analyses are shown in FIG. 5, left panel; and the cell numbers are shown in FIG. 5, right panel. As a result, CHIR99021 was necessary for favorable proliferation of cells, and FGF2, BMP4, VEGF, CHIR99021 and A83-01 were necessary for inducing those cells which were positive for a primitive gut endoderm cell (PGEC) marker CDX2 and negative for definitive endoderm markers CXCR4 and CER1. Therefore, it was revealed that FGF2, BMP4, VEGF, CHIR99021 and A83-01 are essential for the induction of PGEC.

*P1: passage 1. M1-M8: difference in medium composition (#1-#8) is shown. Medium compositions are indicated beneath individual photographs.

Figure 6:
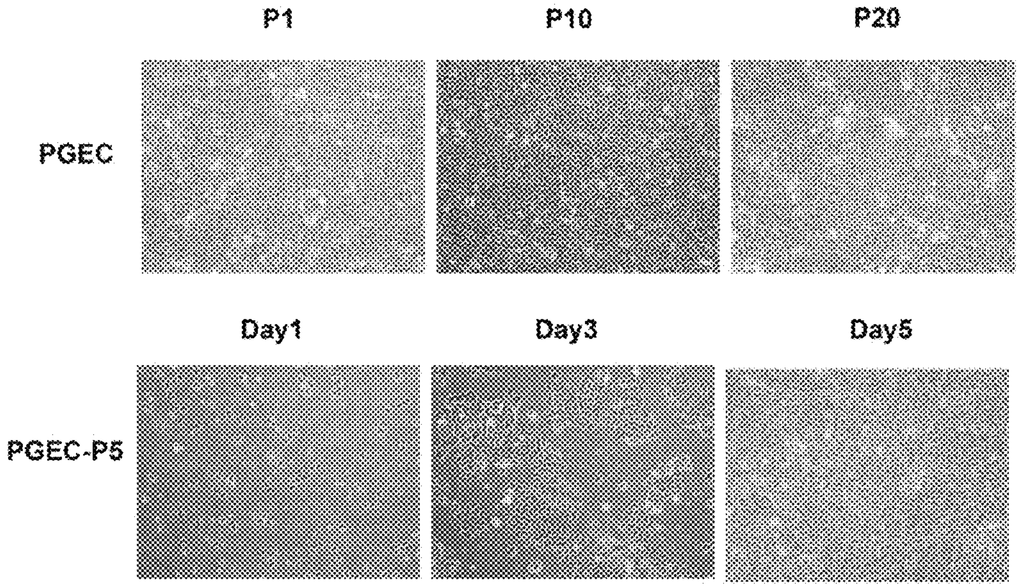
FIG. 6 shows the results of microscopic observations of morphological changes in PGECs after 1 to 20 passages and after 5 passages; cell morphology was retained even after repeating passages over a long period of time.

(5) Morphological observation of PGEC after repeated passaging (FIG. 6). The upper panel of FIG. 6 shows the results of observation of cultured cells on Day 5 after passaging at the stage ofs PGEC-P1, P10 and P20. It was confirmed that, when amplified in the presence of FGF2, BMP4, VEGF, CHIR99021 and A83-01, cell growth continued and an epithelium-like structure characteristic of PGEC was retained even after passaging was repeated more than 20 times. The lower panel of FIG. 6 shows the process of proliferation from Day 1 to Day 5 after passaging at the stage of P5.

*P1: passage 1. M1-M8: difference in medium composition (#1-#8) is shown. Medium compositions are indicated beneath individual photographs.

Figure 7:
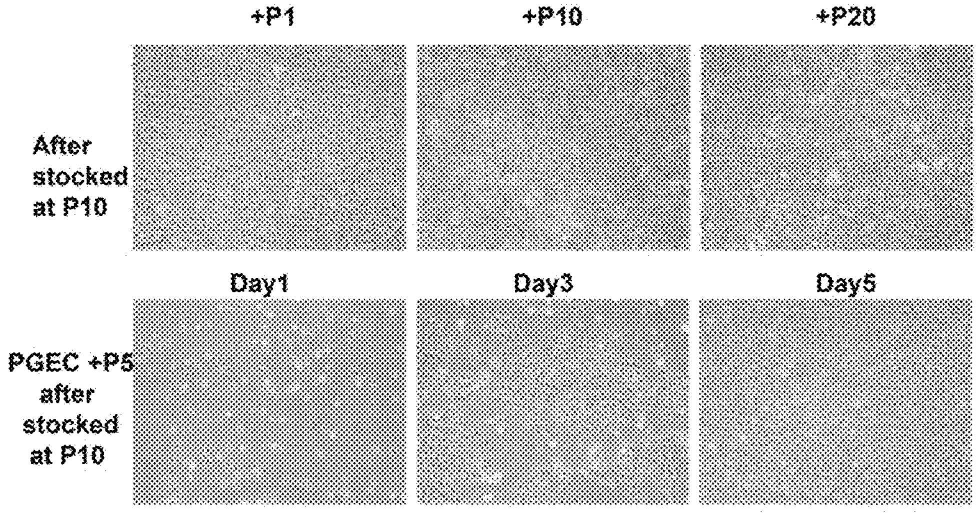
FIG. 7 shows the results of morphological observations of PGECs cryopreserved at passage 10, stored for a long period, thawed and cultured thereafter; cell morphology was retained even after repeating 20 passages after the thawing.

Further, the cells of the present invention permit cryopreservation at an arbitrary timing by the procedures described above in Methods; it has been revealed that cells stocked at P10 for three months can be further amplified for about 20 passages after thawing (FIG. 7). The upper panel of FIG. 7 shows the morphology of PGECs which were stocked and thawed at P10, further passaged once (P1), 10 times (P10) or 20 times (P20) and then amplified on Day 0. In any of the views, epithelium-like cell growth similar to that observed in non-cryopreserved PGECs could be confirmed. The lower panel of FIG. 7 shows the morphology of PGECs which were stocked and thawed at P10, further passaged 5 times (P5) and then amplified on Day 1, Day 3 and Day 5. Obviously, cell growth capacity was also retained favorably.

(6) Cell growth curve (FIG. 8, left) and cell doubling time (FIG. 8, right) of human iPS cell-derived PGECs. These results revealed that at least 20 passages were possible and even frozen (stocked) cells could be passaged 20 times or more.

Figure 9:
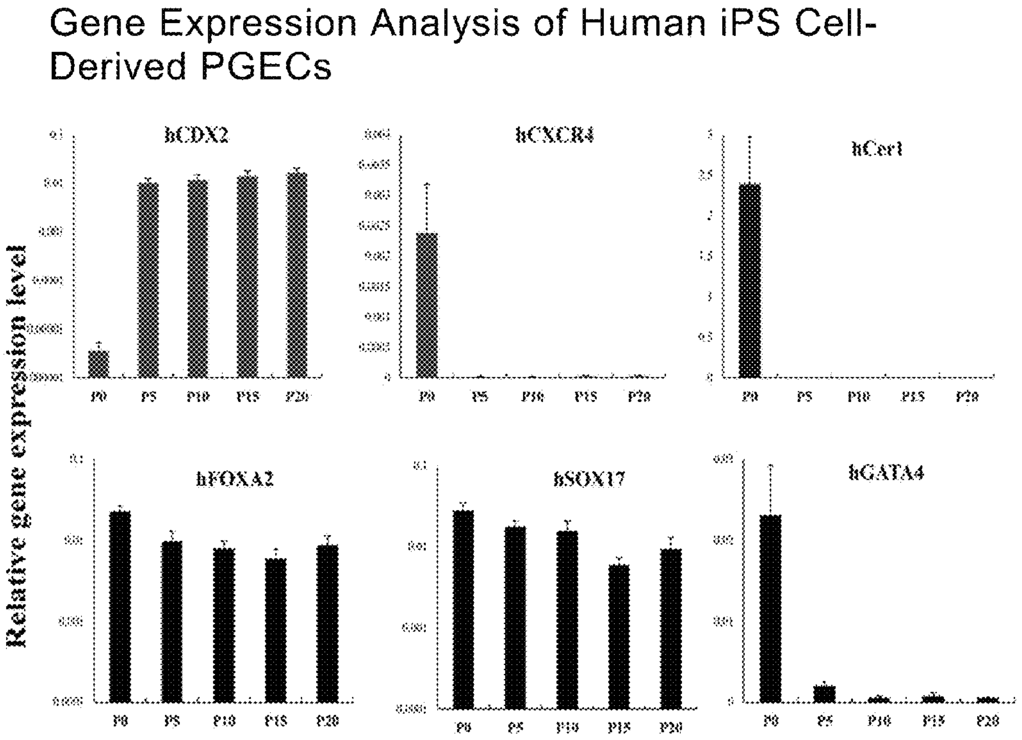
FIG. 9 shows the results of gene expression analyses of human iPS cell-derived PGEC markers before passage (P0) and after passages (P5, 10, 15, 20).

(7) Expression analysis of PGEC marker genes before passage (P0) and after passages (P5, P10, P15 and P20). Cells after passages (P5, P10, P15 and P20) were $CDX2^{+}$/$CER1^{-}$/$CXCR^{-}$ (FIG. 9). Endoderm markers SOX17 and FOXA2 were maintained. Endoderm marker GATA4 was not maintained.

Figure 11:
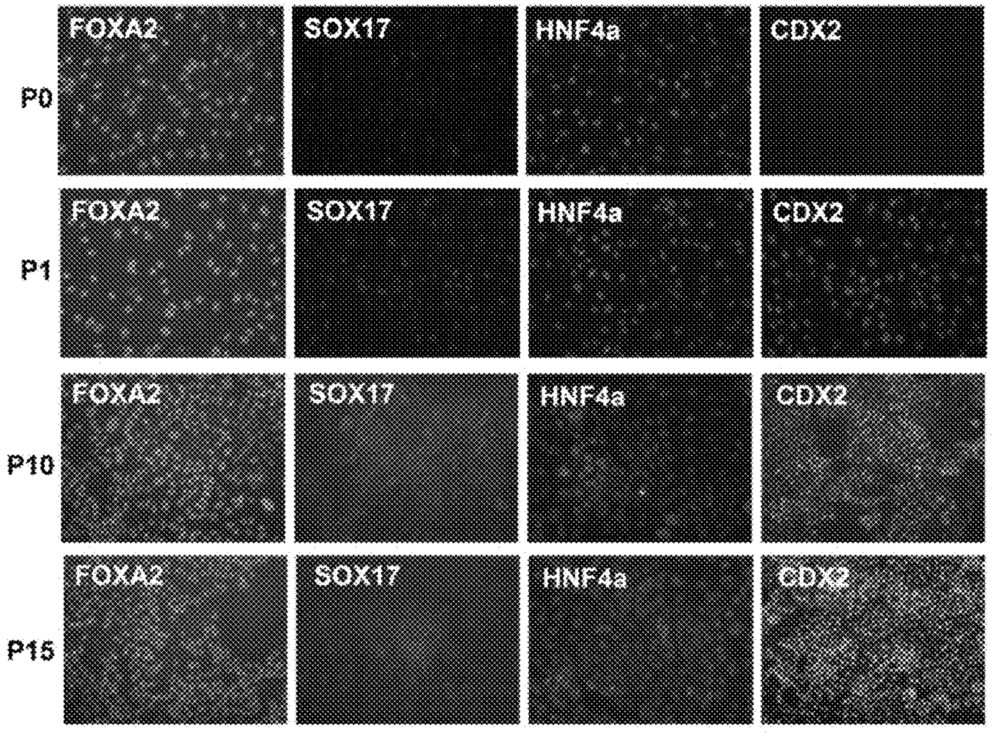
FIG. 11 shows the results of immunological analyses of human iPS cell-derived PGECs before passage (P0) and after passage(s) (P1, 10, 15).
Figure 12:
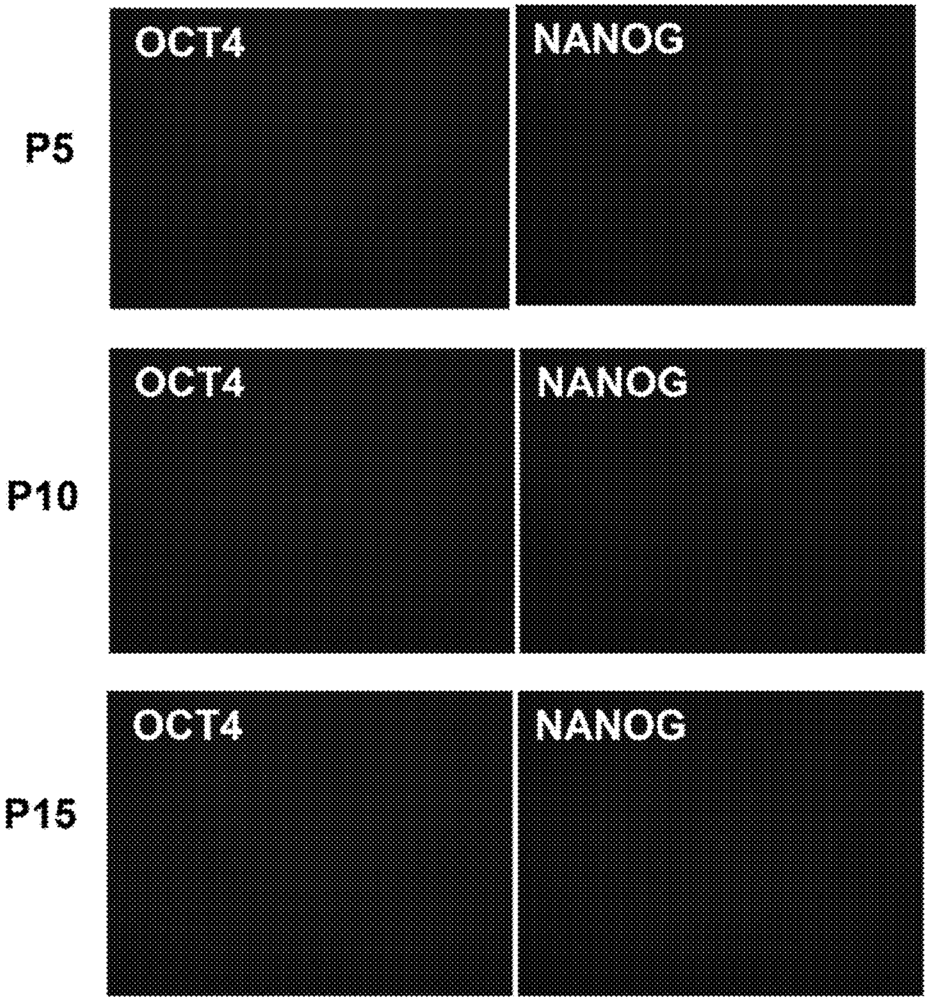
FIG. 12 shows the results of immunological analyses of human iPS cell-derived PGECs after passages (P5, 10, 15).

(8) Analysis of cell properties before passage (P0) and after passages (P1, P10, P15 and P20). The results of FACS (flow cytometry) analysis revealed that cells before passage (P0, Day 5) were mostly positive for both C-KIT and CXCR4 (endoderm progenitor or definitive endoderm markers) whereas cells after passages (P5 and P15) were negative for those markers (FIG. 10). As a result of immunostaining, the PGEC marker CDX2 was not expressed before passage (P0) but after passages (P1, P10 and P15), the cells remained positive for CDX2 (FIG. 11). On the other hand, the cells were positive for endoderm markers FOXA2, SOX17 and HNF4. Further, the cells were negative for pluripotent stem cell markers NANOG and OCT4 (FIG. 12).

(9) In the co-culture [with HUVECs (Lonza, cat. no. 191027) and hMSCs (Lonza, cat. no. PT-2501)], enhanced expressions of genes characteristic of liver buds (such as Alb, TTR) were not observed when not endothelial cell medium used but Hepatocyte Medium (XenoTech) or BMP4- and FGF2-added hepatocyte induction medium (Hepatology, 51(1), 297-305, 2010) was used as a culture broth.

[Example 2] Detailed Analysis of Differentiation Stages by Microarray Analysis

[Experimental Methods]

Total RNA was prepared from human iPSC-PGEC-derived cells [PGEC (P0), PGEC (P1 to P16) and hepatocytes induced from PGEC (PGEC-MH) (the cell obtained in Example 3 described later by directed differentiation)] using RNeasy Mini Kit (Qiagen, Valencia, Calif.). As control group, RNA was obtained from human iPSC-derived cells (hiPSC, iPSC-DE (Definitive Endoderm), iPSC-HE (Hepatic Endoderm) iPSC-IH (Immature Hepatocyte), iPSC-MH (Mature Hepatocyte), iPSC-LB (Liver Bud) (the definition of each cell is described in the following two papers: Si-Tayeb, K. et al. Highly efficient generation of human hepatocyte-like cells from induced pluripotent stem cells. Hepatology 51, 297-305 (2010), Takebe, T. et al. Vascularized and functional human liver from an iPSC-derived organ bud transplant. Nature 499, 481-484 (2013), Takebe, T. et al. Generation of a vascularized and functional human liver from an iPSC-derived organ bud transplant. Nature protocols 9, 396-409 (2014)) and human adult liver (Lot No.: B308121, Biochain Institute, Hayward, Calif., USA), and subjected to analysis. cRNA was amplified, labeled with Low Input Quick Amp Labeling Kit (Agilent Technologies, Palo Alto, Calif.), and hybridized to 44K 60-mer oligomicroarray (Human Gene Expression 4x44K v2 Microarray Kit; Agilent Technologies) according to the manufacturer's instructions. The hybridized microarray slide was scanned with Agilent High-Resolution Microarray Scanner. Relative hybridization intensities and background hybridization values were calculated with Feature Extraction Software version 10.7.3.1 (Agilent Technologies). According to the procedures recommended by Agilent Technologies and using flag criteria in GeneSpring 11.5.1 Software, raw signal intensities and flags of individual probes were calculated from hybridization intensities and spot information. Further, raw signal intensities of samples were processed for log 2 conversion and normalized with quantile algorithm. The present inventors selected probes for every sample except for compromised flag and obtained 34,183 probes as detected genes. From the resultant expression data, differentiation stages of samples were classified by principal component analysis and hierarchical clustering using 75% shiftile & median corrected data.

[Experimental Results]

Figure 13:
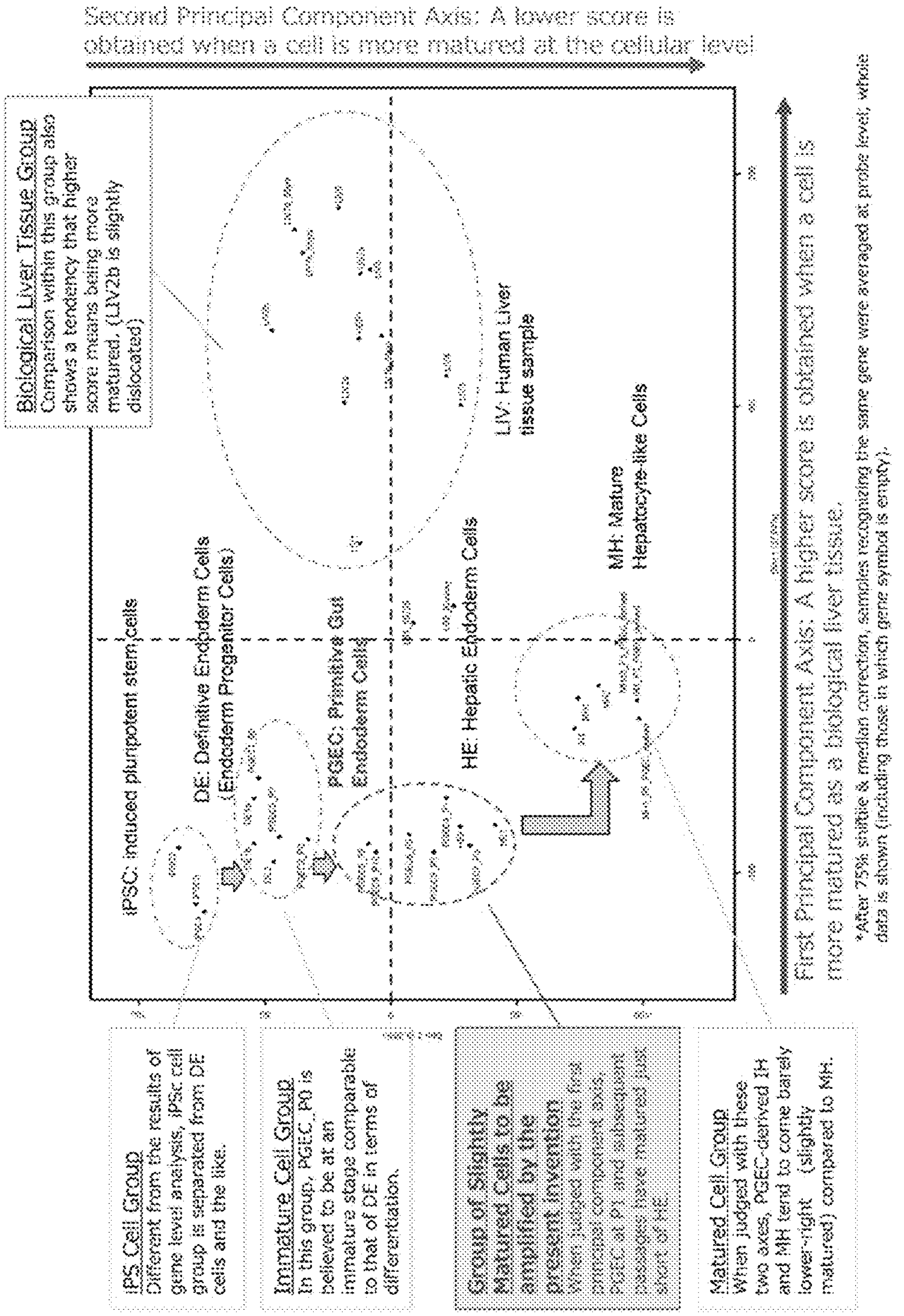
FIG. 13 shows the results of principal component analyses of human iPS cell-derived PGECs.
Figure 14:
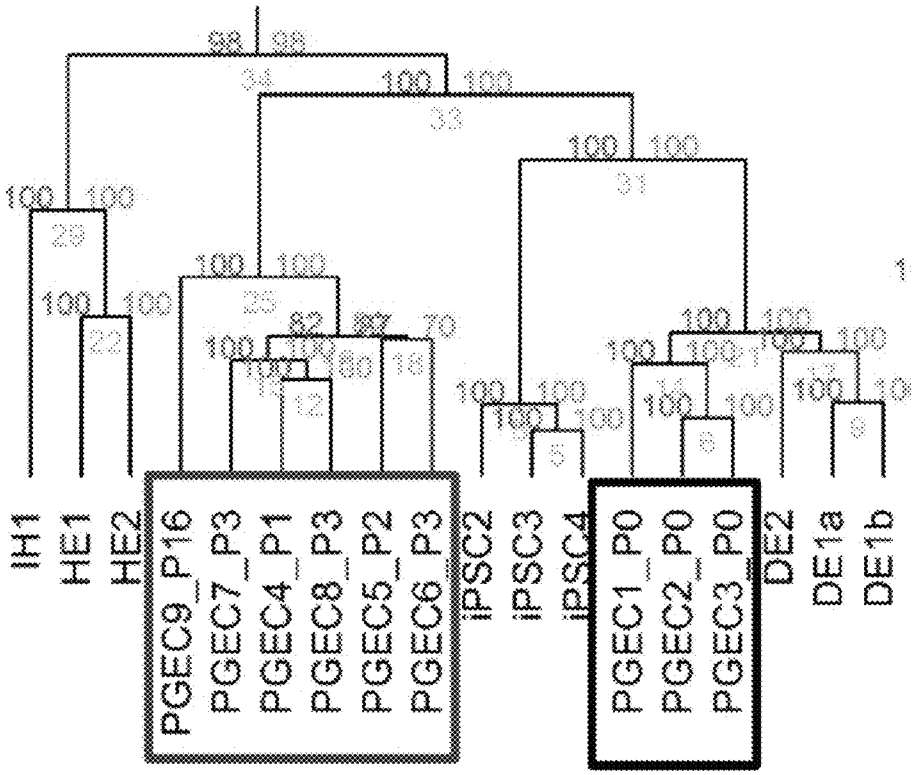
FIG. 14 shows the results of hierarchical clustering analyses of human iPS cell-derived PGECs.

The results of principal component analysis (FIG. 13) and the results of hierarchical clustering (FIG. 14) are shown. It was found that PGECs before passage (P0) are cells corresponding to iPSC-DE (Definitive Endoderm and Endodermal Progenitor). On the other hand, it was shown that cells after passages (P1 to P15) are in a differentiation stage close to iPSC-HE and are in a stage earlier than to the more differentiated iPSC-MH and PGEC-MH. These results revealed that cells amplified after passaging (even once) are cells present in a differentiation stage between iPSC-DE and iPSC-HE.

[Example 3] Differentiation from PGECs into Hepatocytes

[Experimental Methods]

PGECs (P6) were seeded in Matrigel™-coated dishes using—PGE maintenance medium supplemented with Rock Inhibitor (10 μM) so that cells would reach 60-100% confluence on the next day. After confirming 60-100% cell confluence on the next day, the medium was exchanged with Activin (100 ng/ml)-added PGE maintenance medium, followed by two-day culture (PGEC-2d). (When cells have not reached 60% confluence, medium exchange is carried out with PGE maintenance medium, in which cells are cultured until they reach 60% or more confluence.) Subsequently, the medium was exchanged with SFD medium supplemented with DM31898 (250 nM), IWP2 (4 μM), PD0325901 (500 nM) and RA (2 μM), followed by one day culture. Further, the medium was exchanged with SFD medium supplemented with A-83-01 (1 μM), BMP4 (10 ng/ml), IWP2 (4 μM) and RA (2 μM), followed by three-day culture (PGEC-HE). Then, the medium was exchanged with knockout D-MEM medium supplemented with 20% KSR, 1% DMSO, 1% NEAA, 2-ME (0.1 mM) and L-Glutamine (1 mM), followed by three-day culture. Subsequently, HCM was prepared, with EGF removed. To the resultant medium, 5% FBS, HGF (20 ng/ml), OSM (20 ng/ml) and DEX (100 nM) were added. Cells were then cultured for 8 days until they were terminally differentiated and induced into hepatocytes (PGEC-MH).

[Experimental Results]

Figures 1, 15:
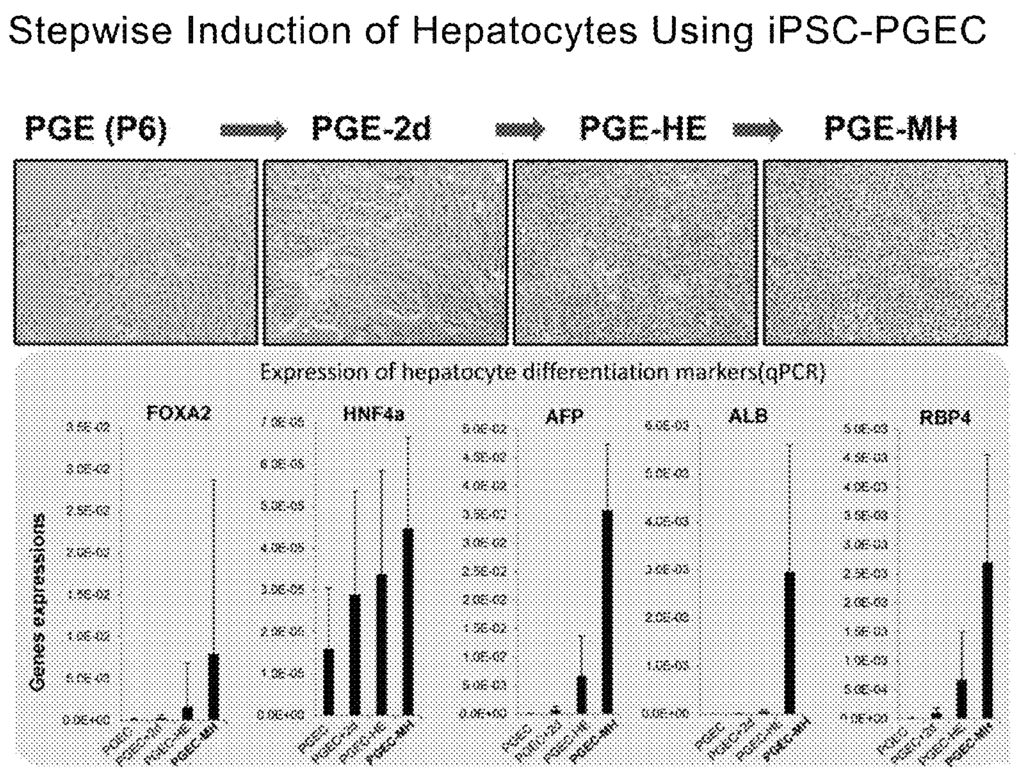
Figures 2, 15:
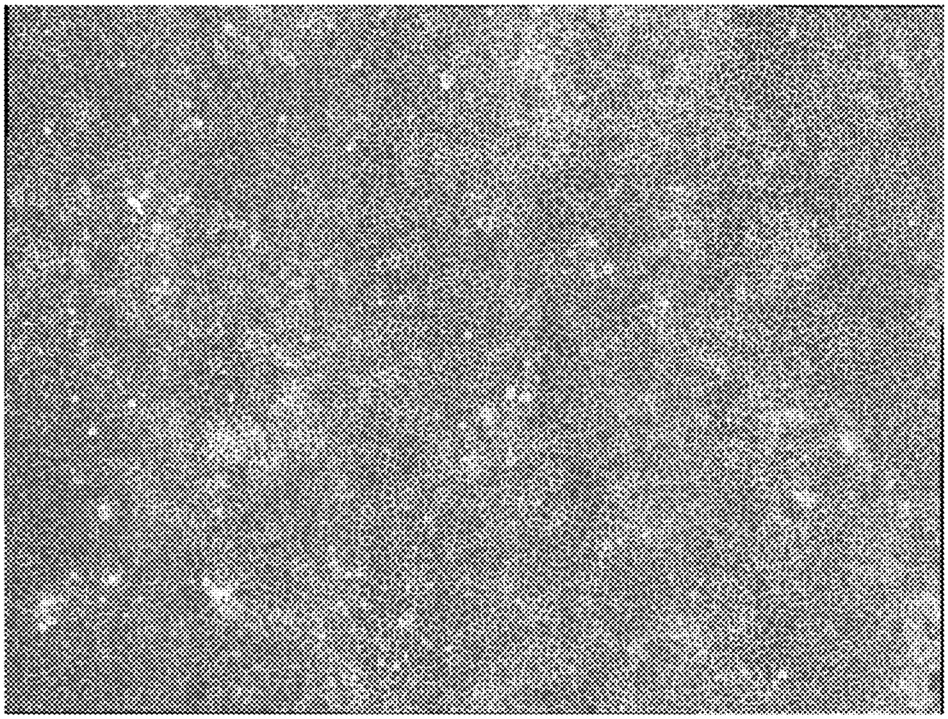
Figure 16:
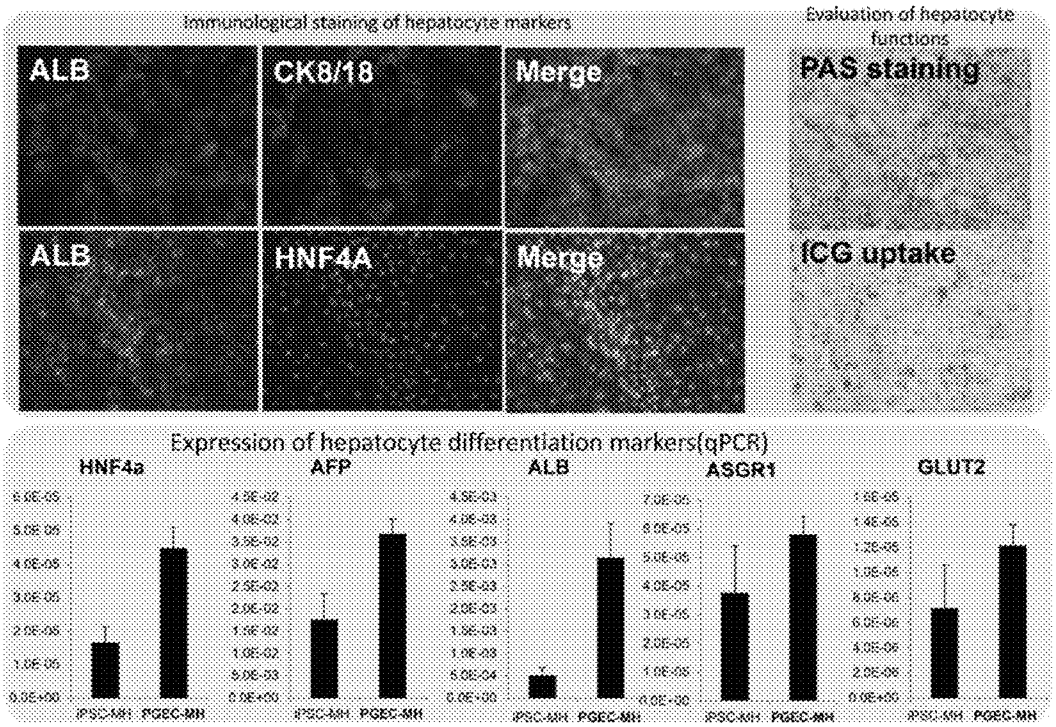
FIG. 16 shows the results of immunological analyses of hepatocytes (PGEC-MH) differentiated and induced from human iPS cell-derived PGECs (upper panel: left), the results of ICG test and PAS staining (upper panel: right), and expressions of hepatocyte differentiation markers (qPCR).

(1) Morphological changes (FIG. 15-1, upper panel) and gene expression analysis (FIG. 15-1, lower panel) of hepatocytes differentiated and induced from amplified PGEC (P6) in a stepwise manner. It was confirmed that terminally differentiated PGEC-MH presented a hepatocyte-like morphology and that expression of hepatocyte marker genes was enhanced. As a result of immunostaining, expression of hepatocyte markers was observed in PGEC-MH. Further, the results of ICG test and PAS staining also revealed that PGEC-MH is a stem cell with a metabolic function (FIG. 16, upper panel).

(2) Usually, it is difficult to homogeneously differentiate and induce hepatocytes from iPSC. However, cells differentiated from PGEC were such that they could be differentiated and induced into hepatocytes having homogeneous morphological features (FIG. 15-2). Therefore, as a result of gene expression analysis, it became clear that hepatocyte markers were expressed significantly higher in PGEC-MH than in MH induced from iPSC (iPSC-MH) (FIG. 16, lower panel).

Figures 1, 17:
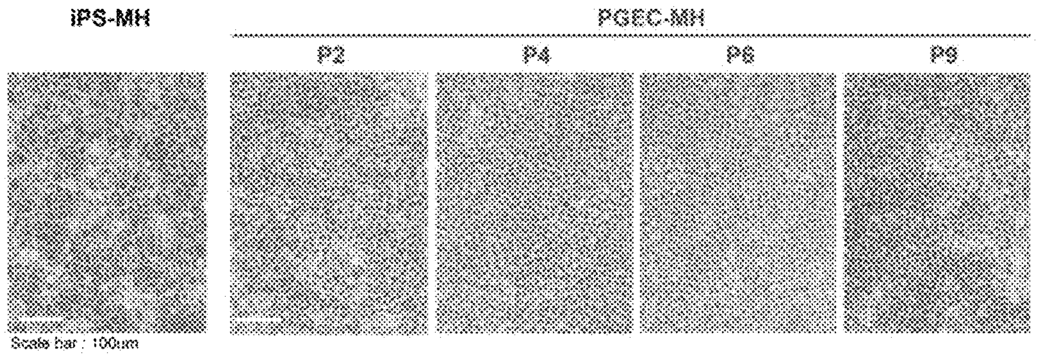
Figures 2, 17:
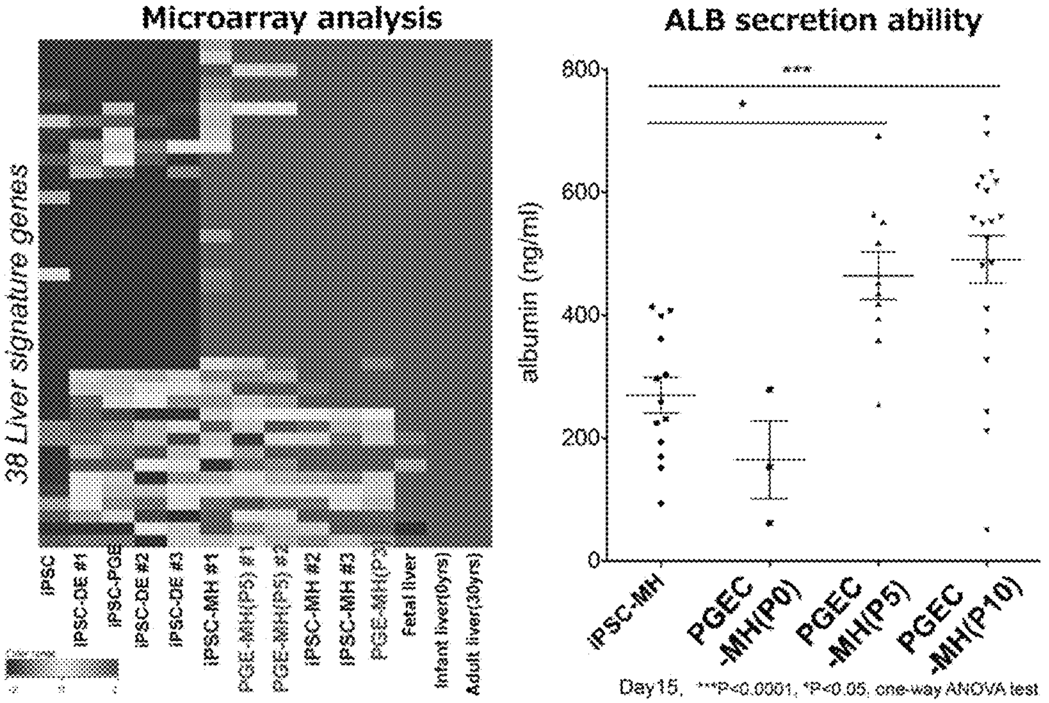

(3) A review of the capacity of passaged PGECs to be differentiated and induced into hepatocytes (FIG. 17). The results of morphological analysis revealed that, even after repeated passaging, PGECs are capable of inducing hepatocytes with good reproducibility (FIG. 17-1). Further, the results of gene expression analysis and protein secretion ability analysis by ELISA revealed that high hepatocyte functions are exhibited even after repeated passaging and that such functions are significantly higher than those seen in iPSC-MH (FIG. 17-2). Interestingly, PGECs (P5 and P10) had higher ALB secretion abilities than PGECs (P0), suggesting that PGECs (P5 and P10) have higher capacity to differentiate into hepatocytes (FIG. 17-2, right).

[Example 4] Differentiation from PGECs into Pancreatic Cells

Figure 18:
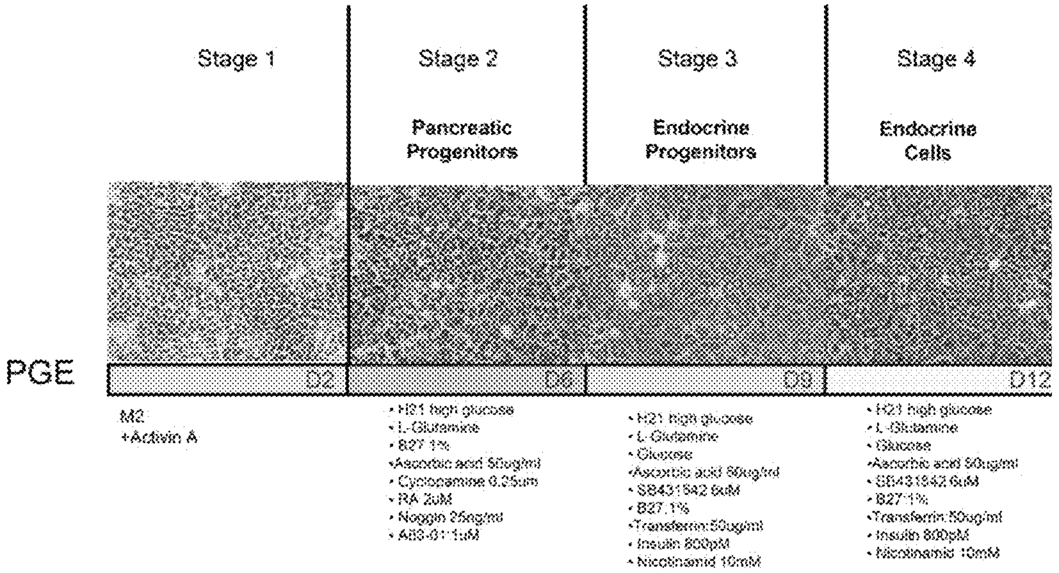
FIG. 18 shows the results of morphological analyses of pancreatic cells induced stepwise from human iPS cell-derived PGECs.

[Experimental Methods] Method of Stepwise Induction of Pancreatic Cells using PGECs (FIG. 18)

Amplified PGECs were seeded in Matrigel™-coated dishes using Rock Inhibitor (10 nM)-added PGEC maintenance medium so that cell density would be about 60-100% on the next day. After confirming 60-100% cell confluence on the next day, the medium was exchanged with Activin (100 ng/ml)-added PGEC maintenance medium, followed by two-day culture. (When cells have not reached 60% confluence, medium exchange is carried out with PGE maintenance medium, in which cells are cultured until they reach 60% or more confluence.) Subsequently, the medium was exchanged with DMEM (high glucose) medium supplemented with L-glutamine (2 mM), B27 (1%), ascorbic acid (50 μg/ml), Noggin (25 ng/ml), A83-01 (1 μM), RA (2 μM) and cyclopamine (0.25 μM), followed by three-day culture. Further, medium exchange was carried out with DMEM (high glucose) medium supplemented with L-glutamine (2 mM), B27 (1%), ascorbic acid (50 μg/ml), Noggin (25 ng/ml), SB431542 (6 μM), insulin (800 μM) and nicotinamide (10 mM), followed by one day culture. Subsequently, the cells were cultured in DMEM (high glucose) medium supplemented with L-glutamine (2 mM), glucose (20 mM), ascorbic acid (50 μg/ml), SB431542 (6 μM), 2-M insulin (800 pM) and nicotinamide (10 mM) for 12 days until they were terminally differentiated and induced into pancreatic cells.

[Experimental Results]

(1) Morphological analysis of pancreatic cells induced stepwise from PGECs (FIG. 18). Differentiation and induction protocol from PGECs to pancreatic cells, in particular, insulin-secretion cells is shown (FIG. 18). Briefly, PDX1-positive pancreatic progenitor cells were induced by culturing PGE-2d in the presence of Noggin, KAAD-cyclopamine and retinoic acid (NCR) for three days. Further, from Day 6 to Day 1, the progenitor cells were cultured in H21 (high glucose) medium containing cited factors such as B27 2. At the stage of Day 12, induction into pancreatic cells was confirmed.

Figure 19:
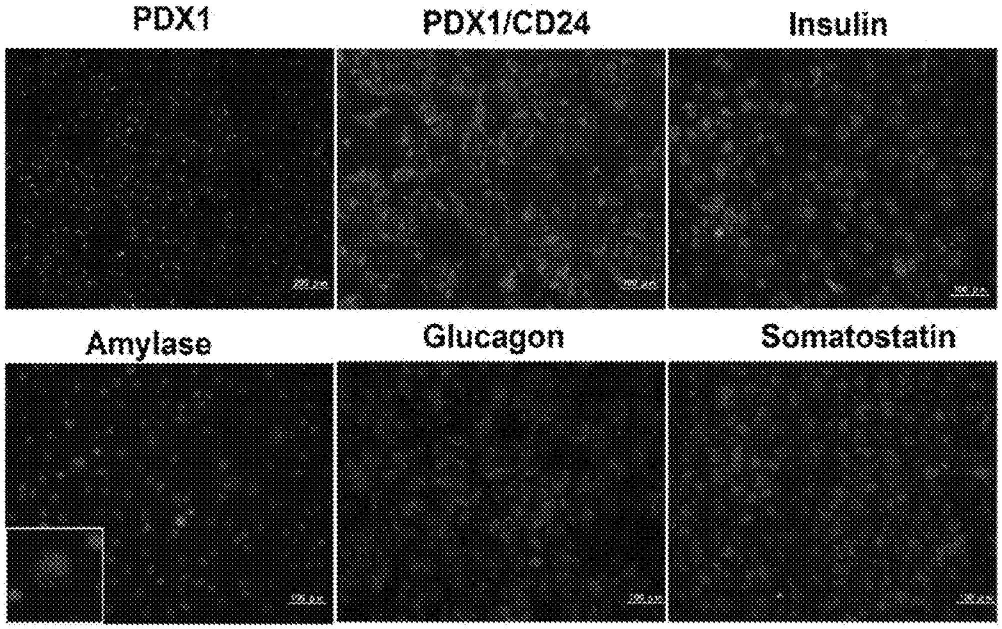
FIG. 19 shows the results of immunostaining of pancreatic cells differentiated and induced from human iPS cell-derived PGECs.

(2) The results of immunostaining showed that PGEC-derived cells had been induced into cells that were positive for pancreatic progenitor marker PDX1, endocrine cell markers INSULIN, GLUCAGON and SOMATOSTATIN, and exocrine cell marker AMYLASE (FIG. 19).

Figure 20:
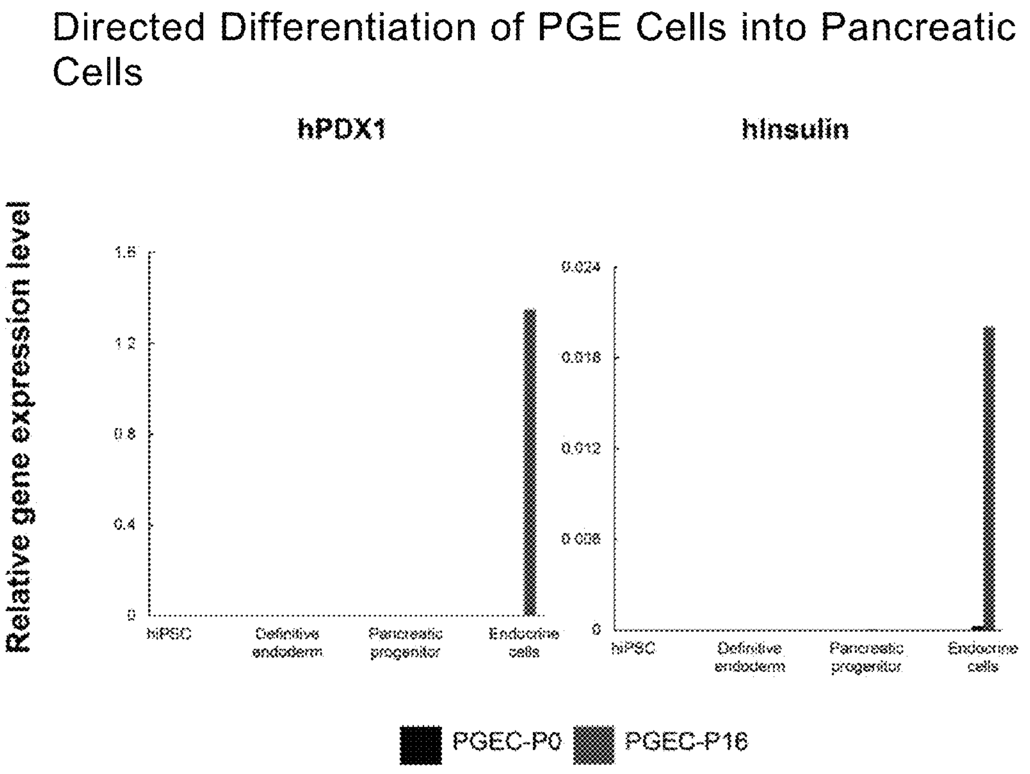
FIG. 20 shows the results of gene expression analysis of pancreatic cells differentiated and induced from human iPS cell-derived PGECs.

(3) The results of gene expression analysis showed enhanced expression of INSULIN and PDX1, thus confirming differentiation and induction into β cells (FIG. 20).

[Example 5] Differentiation from PGECs into Intestinal Tissues

Figure 21:
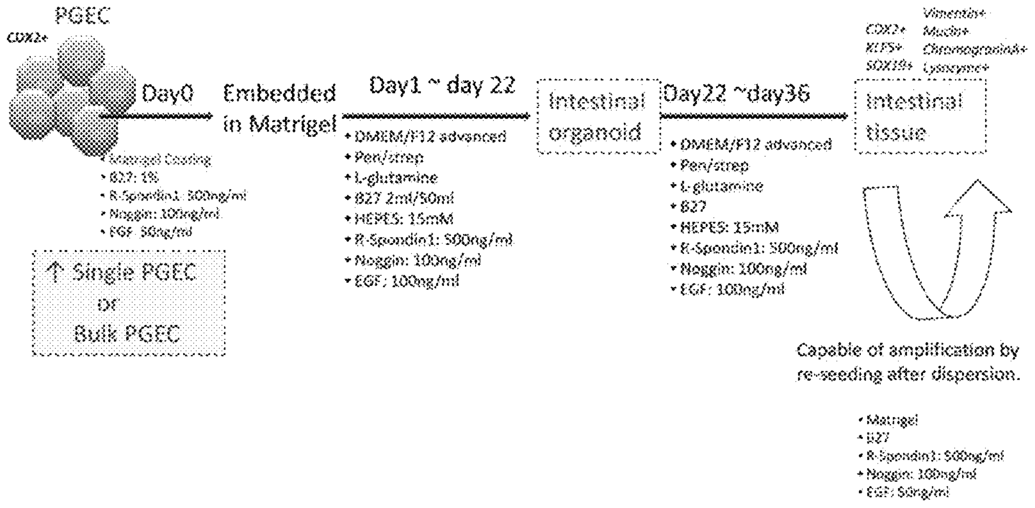
FIG. 21 shows an outline of a method for inducing intestinal tissues stepwise using PGECs.

[Experimental Methods] Method of Stepwise Induction into Intestinal Tissues Using PGECs (FIG. 21)

Using Rock Inhibitor (10 nM)-added PGEC maintenance medium, amplified PGECs were seeded in dishes pre-coated with Matrigel™ containing B27 1%, R-Spondin1 (500 ng/ml), Noggin (100 ng/ml) and EGF (50 ng/ml) as indicated in FIG. 21. After seeding, Matrigel™ containing B27 1%, R-Spondin1 (500 ng/ml), Noggin (100 ng/ml) and EGF (50 ng/ml) was added again to embed the cells. Then, the cells were cultured from Day 1 to Day 22 in DMEM/F12 advanced medium containing Pen/strep, L-glutamine, B27 2 ml/50 ml, HEPES (15 mM), R-Spondin1 (500 ng/ml), Noggin (100 ng/ml) and EGF (100 ng/ml). At Day 22, Matrigel™ containing B27 1%, R-Spondin1 (500 ng/ml), Noggin (100 ng/ml) and EGF (50 ng/ml) was added again from the top to thereby embed the cells, which were cultured in the same medium to thereby induce intestinal tissues. Medium exchange was performed once in every two days. It is possible to obtain intestinal tissues by dispersing the resultant tissues at an arbitrary timing and re-seeding them by the same procedures. With respect to the cell number of PGECs necessary for inducing intestinal tissues, it was possible to prepare intestinal tissues either from a single cell or from a plurality of cells.

[Experimental Results]

(1) Intestinal Tissue Induction Protocol from PGECs (FIG. 21)

Figure 22:
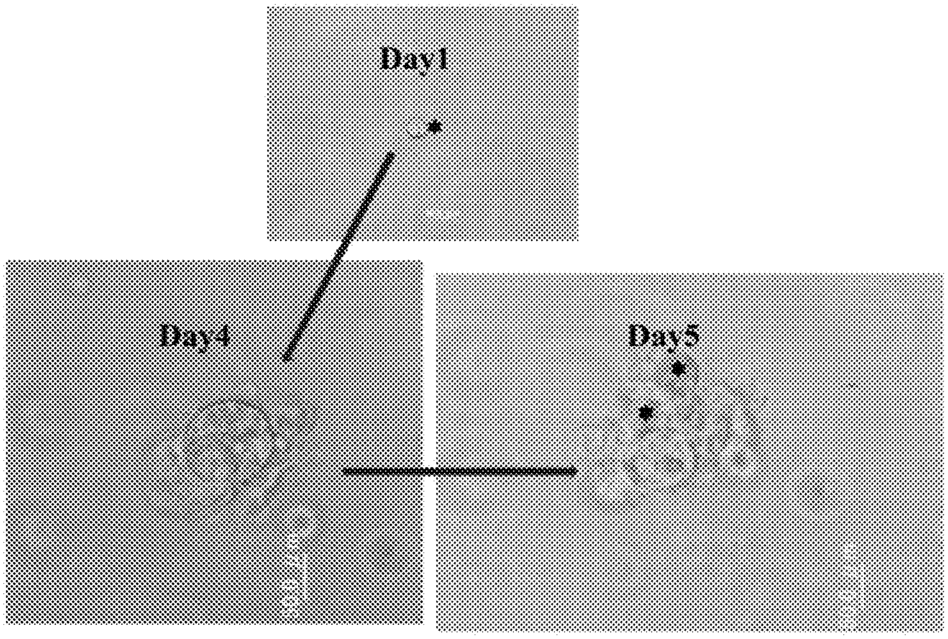
FIG. 22 shows photographs of intestinal tissues induced from PGECs.

(2) The results of microscopic observation revealed that PGECs cultured from a single cell were induced into intestinal tissues presenting a plurality of three-dimensional loop-like structures covered with laminated epithelium (FIG. 22).

Various Measurement Methods Used in Examples 1 to 4

Morphological observation method: FIGS. 2, 4, 6, 15-1 upper panel, 15-2, 17-1 and 18

Observation was made with a phase-contrast microscope (Olympus).

Gene expression analysis of markers: FIGS. 5, 9, 15-1 lower panel, 16-1 and 20

Quantitative real-time reverse transcription PCR (QRT-PCR) was performed with LightCyclera 480 System (Roche) and LightCyclera 480 SYBR Green I Master mix (Roche).

Figure 8:
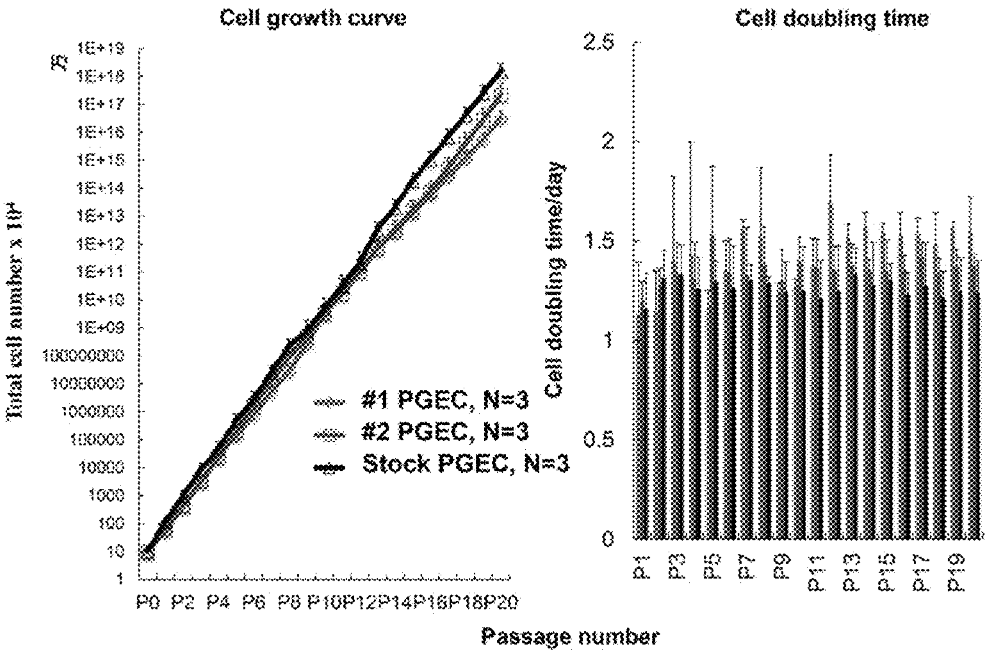
FIG. 8 shows the cell growth curve (left panel) and the cell doubling time (right panel) of human iPS cell-derived PGECs.

Cell growth curve: FIG. 8, left

Cell growth curves were constructed by repeating the following operations. Briefly, cells were seeded so as to give a density of $10^5$ cells/well (6-well plate) (DO) immediately after passaging/seeding. On the third day after seeding, cells were dissociated and counted.

Cell doubling time: FIG. 8, right

A fitted curve was obtained from a growth curve by linear approximation; cell numbers at any two timings were determined from the slope of the fitted curve and substituted into the following calculation formula:

$(t_2-t_1)/3.32\times(\log n_2-\log n_1)$ where $t$ is time and $n$ is cell number.

FACS analysis: FIG. 10

FACS analysis was performed according to the method described in Takebe, T. et al. Vascularized and functional human liver from an iPSC-derived organ bud transplant. Nature 499, 481-484 (2013). Briefly, dissociated cells (definitive endoderm/PGEC) were incubated with fluorescence-conjugated monoclonal antibodies (mAbs) at 4° C. for 30 min in dark, washed with 2% FBS-containing PBS, and analyzed with MoFlo (Dako Cytomation). The antibodies used were allophycocyanin (APC)-conjugated hCD117 (hC-KITAPC) and phycoerythrin (PE)-conjugated hCD184 (hCXCR4PE).

Immunostaining of markers: FIGS. 11, 12, 16 and 19

Cultured cells were fixed with methanol for 30 min on ice, followed by blocking with 10% normal goat serum (NGS) for 60 min. After addition of primary antibody (1:200), cells were incubated at 4° C. overnight. After cells were washed with PBS, appropriate secondary antibodies (e.g., Alexa-488, -555, or -647-conjugated secondary antibodies (1:500; Invitrogen)) were prepared and added to the cells, followed by reaction at room temperature for 60 min. Stained cells were subjected to nuclear staining (DAPI) and embedded in FA mounting fluid. Photographs were taken with Zeiss AxioImager and microscope.

PAS staining: FIG. 16, right upper panel

Giemsa and Periodic Acid Schiff (Wako) staining was performed according to the method in the attached instructions.

ICG uptake: FIG. 16, right lower panel

Cardiogreen reagent (Sigma Cat# I2633) which had been stocked at a concentration of 25 mg/ml with DMSO was diluted with a cell culture medium (DMEM) to give a concentration of 1 mg/ml (working concentration). PGEC-MH in culture were incubated in the previously prepared DMEM medium (1 mg/ml cardiogreen (500 μl/24 well)) at 37° C. for 3-6 hrs. Subsequently, the medium was exchanged with conventional cell culture medium, followed by confirmation of ICG uptake by microscopic observation.

Measurement of ALB secretion ability: FIG. 17, right

Measurement of ALB secretion was performed according to the method described in Takebe, T. et al. Vascularized and functional human liver from an iPSC-derived organ bud transplant. Nature 499, 481-484 (2013). Briefly, after medium exchange, the medium of Day 1 was collected. ALB was measured with Human Albumin ELISA Quantitation Kit (Bethyl Laboratories) according to the methods described in the manufacturer's instructions.

[Example 6] Specific Markers after Passage 1

Figure 23:
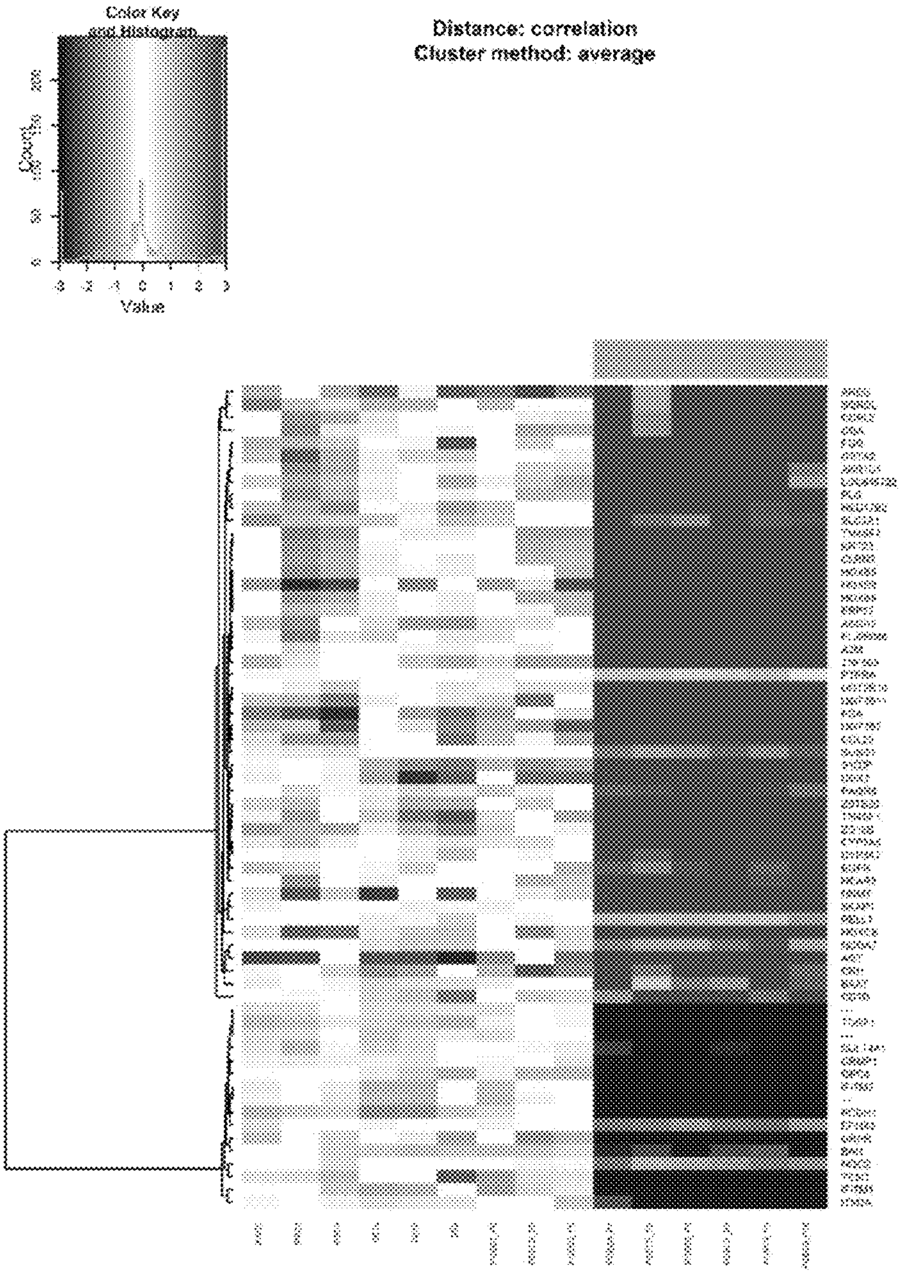
FIG. 23 shows the extraction of positive and negative markers specific to PGECs (P1 and thereafter), with the expression levels of markers specific to human iPS cell-derived PGECs after one passage and thereafter being determined by relative quantification. Positive markers are shown in red and negative markers in blue.

Based on the results of comprehensive expression analyses of all genes obtained by the method described in Example 2, marker genes in iPSC, DE and PGEC (P0) that showed largest expression increase or decrease specifically in PGECs (P1 and thereafter) were extracted (Table 5 and FIG. 23). Briefly, a list of those marker genes which exhibited high expression or low expression across all PGEC (P1 and thereafter) samples is shown.

| Probe ID | GENE SYMBOL | GENE NAME | iPSC2 | iPSC3 | iPSC4 | DE1a | DE1b | DE2 | PGEC1_P0 | PGEC2_P0 |
|---|---|---|---|---|---|---|---|---|---|---|
| A_23_P116898\|2 | A2M | alpha-2-macroglobulin | 0.035484 | −0.61909 | −0.1075 | −0.10649 | −0.2906 | −0.3307 | −0.07321 | −0.36372 |
| A_23_P100730\|8631 | SKAP1 | src kinase associated phosphoprotein 1 | −0.33923 | 0.021544 | −0.15649 | −0.00168 | −0.38794 | −0.29911 | −0.35936 | −0.0166 |
| A_23_P42386\|1081 | CGA | glycoprotein hormones alpha polypeptide | 0.020583 | −1.42989 | −0.46081 | −0.3081 | −0.16563 | −0.27346 | 0 | −1.06523 |
| A_33_P3555368\|440129 | FLJ26086 | hypothetical LOC440129 | −0.28646 | −1.58682 | 0.530572 | −0.63231 | −0.10928 | −0.45405 | −0.44088 | 0 |
| A_23_P139687\|121506 | ERP27 | endoplasmic reticulum protein 27 | 0 | −0.93978 | −0.74333 | −0.31258 | −0.13138 | −0.33445 | −0.05141 | 0.350316 |
| A_23_P8801, A_33_P3249746\|1577 | CYP3A5 | cytochrome P450, family 3, subfamily A, polypeptide 5 | −0.42486 | −0.89161 | −0.30446 | 0.078463 | −0.33589 | −0.56999 | −0.46358 | −0.55576 |
| A_23_P370588\|3218 | HOXB8 | homeobox B8 | 0.029264 | −1.38576 | −1.05356 | −0.31304 | −0.12796 | −0.35383 | 0 | −1.03568 |
| A_23_P358917, A_33_P3318117\|1551 | CYP3A7 | cytochrome P450, family 3, subfamily A, polypeptide 7 | −0.00225 | −0.29894 | 0.018116 | −0.13022 | −0.34804 | −0.80899 | 0 | −0.27573 |
| A_23_P7342\|7365 | UGT2B10 | UDP glucuronosyl-transferase 2 family, polypeptide B10 | −0.17209 | −0.37139 | −0.74064 | 0 | 0.189805 | −0.48488 | −0.24138 | −0.54402 |
| A_32_P231617, A_33_P3390057\|4071 | TM4SF1 | transmembrane 4 L six family member 1 | −0.30731 | −1.13435 | 0.111314 | −0.73527 | −1.61288 | −2.07614 | −0.57755 | 0 |
| A_23_P363316\|3215 | HOXB5 | homeobox B5 | 0.038846 | −1.44721 | −1.0945 | −0.34836 | −0.24599 | −0.33265 | 0 | −0.10457 |
| A_23_P127107\|119467 | CLRN3 | clarin 3 | 0 | −1.2037 | −0.98743 | −0.3849 | −0.12831 | −0.3736 | 0.117985 | −0.94581 |
| A_23_P30693\|5340 | PLG | plasminogen | 0 | −1.32798 | −0.9972 | −0.35026 | −0.08841 | −0.35568 | 0.082272 | −0.97135 |
| A_23_P118203\|124220 | ZG16B | zymogen granule protein 16 homolog B (rat) | −1.18651 | −0.99276 | −1.00801 | −0.33502 | −0.91727 | −1.47394 | −0.62838 | 0 |
| A_23_P78248\|25984 | KRT23 | keratin 23 (histone deacetylase inducible) | 0.036822 | −1.38279 | −1.03368 | −0.28154 | −0.14312 | −0.07947 | 0 | −1.01539 |
| A_23_P148088\|2266 | FGG | fibrinogen gamma chain | −0.91567 | −1.04895 | −0.76722 | −0.15607 | −0.22347 | −2.00165 | 0 | 0.82204 |
| A_23_P216610\|64420 | SUSD1 | sushi domain containing 1 | −0.32363 | −0.43596 | −0.56527 | 0.161051 | 0 | −0.08429 | −0.19519 | −0.09489 |
| A_23_P27013\|3219 | HOXB9 | homeobox B9 | −1.20721 | −2.61014 | −2.26942 | 0 | −1.40718 | 0.020502 | −1.17414 | −0.56194 |
| A_23_P130113\|433 | ASGR2 | asialoglycoprotein receptor 2 | −0.86934 | −1.37926 | 0 | −0.59206 | −1.17995 | −1.21705 | −0.53423 | 0.515928 |
| A_23_P214300\|2939 | GSTA2 | glutathione S-transferase alpha 2 | −0.84545 | −1.94804 | −1.05572 | −0.32986 | −0.68594 | −0.74457 | 0 | 0.185607 |
| A_33_P3262495, A_33_P3268695\|84858 | ZNF503 | zinc finger protein 503 | −0.97481 | −0.49595 | 0 | −0.06278 | −0.77548 | −1.03903 | 0.723968 | −1.19929 |
| A_23_P3221\|58472 | SQRDL | sulfide quinone reductase-like (yeast) | −1.53583 | −0.87025 | −0.58567 | −0.99793 | −0.94762 | 0 | −0.83615 | 0.106649 |
| A_33_P3256810\|7104 | TM4SF4 | transmembrane 4 L six family member 4 | 0 | −1.58275 | −1.2329 | 0.022814 | −0.32676 | −0.36709 | −0.12024 | −1.19298 |

-continued

| | | | | | | | | | | |
|---|---|---|---|---|---|---|---|---|---|---|
| A_33_P3249224\|570 | BAAT | bile acid CoA amino acid N-acyltransferase (glycine N-choloyltransferase) | −0.33027 | −0.0257 | −0.28135 | −0.64944 | −0.5188 | −0.59369 | −0.38859 | 0.094682 |
| A_23_P118065\|3294 | HSD17B2 | hydroxysteroid (17-beta) dehydrogenase 2 | −0.84611 | −1.05892 | −1.377 | 0.108172 | −0.30394 | −1.1097 | −0.70712 | −0.03708 |
| A_33_P3418000, A_32_P116206\|768211 | RELL1 | RELT-like 1 | 0.024254 | 0 | −0.1736 | −0.30211 | −0.23538 | −0.65537 | −0.15747 | −0.29353 |
| A_33_P3304501\|1045 | CDX2 | caudal type homeobox 2 | −0.3334 | 0 | 0.312033 | −1.15235 | −2.5068 | −1.99527 | −0.18675 | −1.73892 |
| A_33_P3291154, A_23_P40866\|26137 | ZBTB20 | zinc finger and BTB domain containing 20 | −0.65219 | −0.84965 | −0.03497 | −0.46441 | −1.02571 | −1.01218 | 0 | 0.815232 |
| A_33_P3375541\|915 | CD3D | CD3d molecule, delta (CD3-TCR complex) | 0 | 0.298861 | −0.17901 | −0.6879 | −0.82601 | −1.61039 | −0.0255 | −0.71067 |
| A_24_P334640\|85315 | PAQR8 | progestin and adipoQ receptor family member VIII | −0.01128 | −0.58932 | 0.23462 | −0.32581 | −0.64189 | −0.40645 | −0.79043 | −0.34201 |
| A_23_P69310\|9034 | CCRL2 | chemokine (C-C motif) receptor-like 2 | −0.12023 | −1.37791 | −1.06193 | −0.46476 | −0.18956 | 0 | 0.049263 | −0.30672 |
| A_23_P28869\|5786 | PTPRA | protein tyrosine phosphatase, receptor type, A | −0.24437 | −0.22254 | −0.12723 | −0.08435 | 0 | 0.120167 | −0.38086 | −0.16053 |
| A_33_P3392142, A_23_P382000\|6718 | AKR1D1 | aldo-keto reductase family 1, member D1 (delta 4-3-ketosteroid-5-beta-reductase) | 0 | −1.42915 | −1.08785 | −0.32694 | −0.16398 | −0.34522 | −0.05121 | 0.76792 |
| A_23_P64721\|8843 | HCAR3 | hydroxycarboxylic acid receptor 3 | 0 | −1.31936 | −0.10459 | −0.33615 | −0.12922 | −0.00778 | 0.110513 | −0.94598 |
| A_23_P17065\|6364 | CCL20 | chemokine (C-C motif) ligand 20 | −0.55429 | −1.25318 | −1.213 | 0.195006 | 0 | −1.64729 | −0.80351 | −0.20712 |
| A_23_P259071, A_33_P3419190\|374 | AREG | amphiregulin | −1.06741 | 0 | −1.03385 | −1.75712 | 0.304121 | −1.95908 | −1.63663 | −2.27442 |
| A_24_P896205\|645722 | LOC645722 | hypothetical protein LOC645722 | −0.66543 | −1.15472 | −0.81469 | 0.398036 | 0 | −1.08232 | −0.35942 | −0.77336 |
| A_24_P124558\|3224 | HOXC8 | homeobox C8 | −0.53925 | −1.99415 | −1.63401 | 0.579059 | −0.71201 | −0.8857 | 0 | −1.45446 |
| A_23_P58266\|6286 | S100P | S100 calcium binding protein P | 0.215119 | 0 | −0.27319 | −0.91825 | −1.45162 | −1.61303 | −0.97264 | −1.33731 |
| A_23_P31755\|1392 | CRH | corticotropin releasing hormone | −0.22625 | 0.033955 | −0.63724 | −1.39434 | −1.13463 | 0 | −0.94835 | −2.00196 |
| A_23_P215790, A_33_P3351944, A_33_P3351955\|1956 | EGFR | epidermal growth factor receptor | −0.81339 | −0.60543 | 0 | −0.28022 | −0.63179 | 0.011038 | −0.19497 | −0.05886 |

-continued

| | | | | | | | | | | |
|---|---|---|---|---|---|---|---|---|---|---|
| A_23_P127584\|4837 | NNMT | nicotinamide N-methyl-transferase | −0.51281 | −2.08461 | −0.70741 | −2.42518 | 0 | −1.94237 | −0.12695 | 0.445169 |
| A_33_P3418421, A_24_P217234, A_33_P3418417, A_33_P3418426\|6519 | SLC3A1 | solute carrier family 3 (cystine, dibasic and neutral amino acid transporters, activator of cystine, dibasic and neutral amino acid transport) member 1 | −1.3496 | −0.99492 | −0.77279 | −0.73149 | −0.2713 | −0.88098 | −0.67748 | 0 |
| A_23_P136671\|7364 | UGT2B7 | UDP glucuronosyl-transferase 2 family, polypeptide B7 | −0.95277 | −0.7047 | −2.06734 | 0 | 0.67708 | −1.41199 | −0.97469 | −1.12322 |
| A_23_P212968\|10720 | UGT2B11 | UDP glucuronosyl-transferase 2 family polypeptide B11 | −0.82092 | −0.97144 | −1.62693 | −0.39106 | 0.087372 | −0.46845 | −0.62732 | −1.63843 |
| A_24_P12435\|135112 | NCOA7 | nuclear receptor coactivator 7 | 0 | −0.18129 | 0.002614 | −0.50483 | −0.71161 | −0.74713 | −0.11886 | −0.02634 |
| A_23_P115261\|183 | AGT | angiotensinogen (serpin peptidase inhibitor, clade A, member 8) | −2.27104 | −2.12171 | 0 | −2.09432 | −2.14932 | −2.73508 | −1.34962 | 0.032398 |
| A_23_P44274, A_24_P282251\|2243 | FGA | fibrinogen alpha chain | −1.52852 | −2.00069 | −2.62255 | 0.069209 | −1.14009 | −1.67135 | −1.19804 | 0 |
| A_23_P171074\|9452 | ITM2A | integral membrane protein 2A | 0.229918 | −0.01278 | 0.318004 | 0.665385 | 0.588651 | 0.586195 | 0 | 0.106415 |
| A_23_P132889\|1400 | CRMP1 | collapsin response mediator protein 1 | 0.302726 | 0.424546 | 0.331372 | 0.381194 | 0.522077 | −0.17068 | 0.291908 | 0 |
| A_23_P366376\|6997 | TDGF1 | teratocarcinoma-derived growth factor 1 | 1.055902 | 0.975906 | 0.443375 | 0.7792 | 0.939159 | 1.144099 | 0.340541 | 0 |
| A_33_P3360530 | | | 0.605786 | 0.65743 | 0 | 0.635332 | 0.610539 | 0.576718 | 0.647823 | 0.017088 |
| A_33_P3408034 | | | 0.646906 | 0.614313 | 0 | 0.908723 | 0.667665 | 0.458841 | 0.688125 | 0.056206 |
| A_23_P435407\|2239 | GPC4 | glypican 4 | −0.12283 | 0 | 0.005823 | 0.45027 | 0.861538 | 1.219915 | 0.363876 | 1.061733 |
| A_23_P119593\|79852 | EPHX3 | epoxide hydrolase 3 | 0.64492 | 0.118802 | 0.155959 | 0.348819 | 0.17514 | 0.35963 | 0.385176 | −0.10665 |
| A_23_P72737, A_33_P3423941\|8519 | IFITM1 | interferon induced transmembrane protein 1 (9-27) | 0.105631 | 0.095569 | −0.78524 | 1.255876 | 1.193417 | 0 | 1.413558 | 0.759937 |
| A_23_P58953, A_33_P3773261\|4835 | NQO2 | NAD(P)H , dehydrogenase quinone 2 | 0.013543 | 0.124331 | 0.617963 | −0.18804 | 0 | 0.112679 | 0.122828 | 0.321461 |

-continued

| | | | | | | | | | | |
|---|---|---|---|---|---|---|---|---|---|---|
| A_24_P357266\|2925 | GRPR | gastrin-releasing peptide receptor | −0.80677 | 0 | 0.773735 | 0.025359 | 0.441417 | 1.320668 | 0.035607 | 1.651856 |
| A_33_P3353345, A_33_P3280367\|25830 | SULT4A1 | sulfotransferase family 4A, member 1 | 0.551437 | 1.018361 | 0.287167 | 0.758323 | 0.616955 | 0 | 0.161203 | 0.272604 |
| A-24_P15502 | | | 0.31672 | 0.040735 | −0.47952 | 1.096931 | 1.141647 | 0.152782 | 1.017473 | 0.306318 |
| A_23_P76538\|54997 | TESC | tescalcin | 0.54078 | 0.604147 | 1.073677 | 0 | −0.17079 | 2.423596 | 1.428295 | 0.636807 |
| A_24_P287043\|10581 | IFITM2 | interferon induced transmembrane protein 2 (1-8D) | 0.408745 | 0.068269 | −0.34835 | 1.162954 | 1.138148 | 0.137067 | 0.92231 | 0.161296 |
| A_33_P3285470\|575 | BAI1 | brain-specific angiogenesis inhibitor 1 | 0 | −0.05105 | 0.740587 | 0.877379 | 1.043593 | 0.981359 | 1.087032 | 0.943179 |
| A_33_P3349637, A_24_P234838\|5097 | PCDH1 | protocadherin 1 | 1.14639 | 0.880724 | 0.719095 | 1.730392 | 1.617984 | 0.976905 | 0.615231 | −0.05447 |

| Probe ID | PGEC3_P0 | PGEC4_P1 | PGEC5_P2 | PGEC6_P3 | PGEC7_P3 | PGEC8_P3 | PGEC9_P1 | UP DN | RANK OF ROKU |
|---|---|---|---|---|---|---|---|---|---|
| A_23_P116898\|2 | 0 | 9.59406 | 7.157472 | 7.528813 | 9.860452 | 8.219652 | 6.556471 | UP | 1 |
| A_23_P100730\|8631 | 0 | 3.810782 | 6.201985 | 4.472992 | 3.206003 | 5.065433 | 5.96643 | UP | 2 |
| A_23_P42386\|1081 | −0.99842 | 10.71766 | 1.857644 | 5.788428 | 6.634753 | 4.684488 | 7.532835 | UP | 3 |
| A_33_P3555368\|440129 | −0.18012 | 9.983083 | 8.175266 | 8.641662 | 8.977219 | 10.00043 | 7.684394 | UP | 4 |
| A_23_P139687\|121506 | −0.98907 | 9.228296 | 8.811811 | 8.883856 | 8.268251 | 9.039125 | 8.557015 | UP | 5 |
| A_23_P8801, A_33_P3249746\|1577 | 0 | 4.072534 | 3.200599 | 4.929774 | 4.858568 | 4.303244 | 4.35034 | UP | 6 |
| A_23_P370588\|3218 | −0.92531 | 9.404708 | 10.30383 | 9.793105 | 8.89808 | 9.99541 | 9.997499 | UP | 7 |
| A_23_P358917, A_33_P3318117\|1551 | −0.01001 | 3.309094 | 2.52227 | 4.212578 | 4.022702 | 3.577415 | 3.693563 | UP | 8 |
| A_23_P7342\|7365 | −0.5183 | 4.158992 | 3.185945 | 3.905903 | 4.899543 | 3.221666 | 3.086537 | UP | 9 |
| A_32_P231617, A_33_P3390057\|4071 | −1.03484 | 7.513394 | 8.080159 | 8.867767 | 9.567626 | 8.465519 | 10.48137 | UP | 10 |
| A_23_P363316\|3215 | −0.95228 | 7.04726 | 7.470543 | 5.588046 | 6.209956 | 7.15297 | 6.704992 | UP | 11 |
| A_23_P127107\|119467 | −0.83761 | 6.962229 | 6.551431 | 4.764102 | 6.47516 | 6.083357 | 4.311534 | UP | 12 |
| A_23_P30693\|5340 | −0.8745 | 8.510991 | 5.362725 | 4.437788 | 6.666848 | 3.29827 | 3.723882 | UP | 13 |
| A_23_P118203\|124220 | 0.378361 | 5.464998 | 6.284544 | 6.994697 | 6.694204 | 5.627764 | 7.888292 | UP | 14 |
| A_23_P78248\|25984 | −0.94729 | 8.808288 | 6.028291 | 6.920158 | 6.255255 | 7.542379 | 5.695623 | UP | 15 |
| A_23_P148088\|2266 | −0.17596 | 9.342705 | 7.031907 | 6.834038 | 8.544293 | 6.004672 | 4.109532 | UP | 16 |
| A_23_P216610\|64420 | −0.00838 | 2.128412 | 1.667598 | 1.802901 | 2.445431 | 1.935143 | 2.523052 | UP | 17 |
| A_23_P27013\|3219 | −2.11611 | 10.41891 | 11.20704 | 9.506152 | 9.262839 | 11.66512 | 10.03637 | UP | 18 |
| A_23_P130113\|433 | −0.12342 | 7.014019 | 6.201549 | 5.841208 | 6.829593 | 6.131578 | 4.691435 | UP | 19 |
| A_23_P214300\|2939 | −0.35865 | 5.635105 | 5.279348 | 4.9628 | 5.921765 | 4.410652 | 3.013806 | UP | 20 |
| A_33_P3262495, A_33_P3268695\|84858 | −1.13023 | 7.360002 | 5.773656 | 5.887572 | 5.233572 | 6.636807 | 5.072298 | UP | 21 |
| A_23_P3221\|58472 | −0.17738 | 3.984718 | 1.484224 | 5.391895 | 4.375029 | 4.502015 | 7.972498 | UP | 22 |
| A_33_P3256810\|7104 | −1.1231 | 7.715345 | 5.974287 | 6.129033 | 6.254088 | 6.471998 | 5.271347 | UP | 23 |
| A_33_P3249224\|570 | 0 | 3.236911 | 1.097169 | 2.189851 | 1.859661 | 4.325985 | 2.571649 | UP | 24 |
| A_23_P118065\|3294 | 0 | 7.495122 | 4.423458 | 4.043093 | 6.461859 | 2.75114 | 3.659675 | UP | 25 |
| A_33_P3418000, A_32_P116206\|768211 | −0.1002 | 1.308504 | 1.273732 | 1.391944 | 1.176373 | 1.179655 | 1.784656 | UP | 26 |
| A_33_P3304501\|1045 | −1.78302 | 9.857761 | 9.26749 | 9.236861 | 9.111102 | 9.584235 | 8.491552 | UP | 27 |
| A_33_P3291154, A_23_P40866\|26137 | −0.003 | 4.660577 | 4.117335 | 5.102535 | 5.288275 | 4.811791 | 6.012475 | UP | 28 |
| A_33_P3375541\|915 | −0.51468 | 1.857045 | 3.510579 | 4.033863 | 4.742079 | 2.310155 | 5.770374 | UP | 29 |

-continued

| | | | | | | | | | |
|---|---|---|---|---|---|---|---|---|---|
| A_24_P334640\|85315 | 0 | 2.511047 | 2.745831 | 2.905705 | 3.522153 | 2.834136 | 2.30866 | UP | 30 |
| A_23_P69310\|9034 | −0.4149 | 3.994144 | 1.868846 | 3.169338 | 3.585423 | 4.959897 | 5.158014 | UP | 31 |
| A_23_P28869\|5786 | −0.1162 | 1.103771 | 1.161767 | 0.903581 | 1.079373 | 1.200111 | 0.632035 | UP | 32 |
| A_33_P3392142, A_23_P382000\|6718 | −0.61671 | 5.500243 | 3.637479 | 4.054358 | 6.099155 | 4.047012 | 2.115805 | UP | 33 |
| A_23_P64721\|8843 | −0.719 | 2.94353 | 2.901486 | 3.764475 | 4.253921 | 2.74777 | 3.946737 | UP | 34 |
| A_23_P17065\|6364 | −1.03577 | 4.614782 | 3.961754 | 5.097384 | 5.611992 | 4.692313 | 5.306599 | UP | 35 |
| A_23_P259071, A_33_P3419190\|374 | −1.67856 | 5.493373 | 1.45172 | 6.345245 | 6.856207 | 7.273076 | 9.134583 | UP | 36 |
| A_24_P896205\|645722 | −1.06721 | 4.438249 | 3.631331 | 4.211386 | 4.800885 | 4.27861 | 1.637881 | UP | 37 |
| A_24_P124558\|3224 | −0.6797 | 7.155211 | 6.561634 | 4.355327 | 3.879619 | 7.785979 | 4.129494 | UP | 38 |
| A_23_P58266\|6286 | −1.1063 | 5.261293 | 3.777145 | 5.844682 | 5.185188 | 5.58016 | 4.906141 | UP | 39 |
| A_23_P31755\|1392 | −1.47379 | 6.521231 | 2.146891 | 3.870679 | 4.62909 | 5.690667 | 2.48346 | UP | 40 |
| A_23_P215790, A_33_P3351944, A_33_P3351955\|1956 | −0.96405 | 2.508869 | 2.020423 | 2.722858 | 3.215947 | 2.547208 | 3.044634 | UP | 41 |
| A_23_P127584\|4837 | −0.61342 | 5.73834 | 8.004148 | 6.256389 | 5.681221 | 6.308977 | 8.402271 | UP | 42 |
| A_33_P3418421, A_24_P217234, A_33_P3418417, A_33_P3418426\|6519 | 0.152302 | 3.60197 | 2.303726 | 1.987805 | 3.998466 | 2.677109 | 2.711808 | UP | 43 |
| A_23_P136671\|7364 | −1.92844 | 5.929523 | 5.387286 | 6.229324 | 7.095386 | 4.863998 | 5.771834 | UP | 44 |
| A_23_P212968\|10720 | 0 | 5.363499 | 3.846857 | 4.946187 | 6.432818 | 3.926768 | 3.583979 | UP | 45 |
| A_24_P12435\|135112 | −0.52127 | 2.037577 | 1.577885 | 1.505384 | 2.244186 | 2.744535 | 1.510181 | UP | 46 |
| A_23_P115261\|183 | −1.60228 | 8.573734 | 4.294716 | 5.255239 | 6.486434 | 7.018931 | 3.599419 | UP | 47 |
| A_23_P44274, A_24_P282251\|2243 | −0.50906 | 5.633089 | 5.508142 | 6.252135 | 7.527841 | 4.882538 | 4.416079 | UP | 48 |
| A_23_P171074\|9452 | 0.90552 | −2.29194 | −3.52368 | −5.8367 | −4.2045 | −3.52509 | −8.516 | DOWN | 1 |
| A_23_P132889\|1400 | 0.577018 | −3.87227 | −2.91236 | −4.51907 | −3.12466 | −4.38317 | −3.8124 | DOWN | 2 |
| A_23_P366376\|6997 | −0.20308 | −7.62468 | −8.93359 | −8.90506 | −6.96497 | −7.85155 | −10.2968 | DOWN | 3 |
| A_33_P3360530 | −0.22021 | −4.97088 | −6.19484 | −5.98294 | −5.10492 | −4.84282 | −7.20808 | DOWN | 4 |
| A_33_P3408034 | −0.16218 | −4.84628 | −6.04157 | −5.60335 | −4.88079 | −4.72212 | −6.00471 | DOWN | 5 |
| A_23_P435407\|2239 | 1.199933 | −5.90605 | −6.00413 | −6.93013 | −5.39623 | −6.38798 | −5.82359 | DOWN | 6 |
| A_23_P119593\|79852 | 0 | −1.84214 | −1.78773 | −1.45394 | −1.84792 | −1.91593 | −1.4764 | DOWN | 7 |
| A_23_P72737, A_33_P3423941\|8519 | 0.445076 | −4.62682 | −5.62128 | −5.61057 | −5.32483 | −4.46544 | −8.59465 | DOWN | 8 |
| A_23_P58953, A_33_P3773261\|4835 | 0.283805 | −1.84637 | −1.17777 | −1.21441 | −1.47292 | −1.75658 | −1.59893 | DOWN | 9 |
| A_24_P357266\|2925 | 1.155787 | −4.43356 | −5.95164 | −6.6555 | −5.28831 | −4.03908 | −6.22327 | DOWN | 10 |
| A_33_P3353345, A_33_P3280367\|25830 | −0.37109 | −2.53825 | −3.0892 | −3.28029 | −2.79275 | −3.62165 | −3.19978 | DOWN | 11 |
| A-24_P15502 | 0 | −4.3981 | −3.94634 | −3.33916 | −4.16933 | −4.06356 | −3.89262 | DOWN | 12 |
| A_23_P76538\|54997 | 0.542653 | −4.80006 | −3.75679 | −4.47878 | −4.16871 | −6.09137 | −4.21434 | DOWN | 13 |
| A_24_P287043\|10581 | 0 | −3.9927 | −3.46729 | −2.97456 | −3.77627 | −3.70409 | −3.57571 | DOWN | 14 |
| A_33_P3285470\|575 | 0.648405 | −2.78643 | −2.32866 | −3.49812 | −2.37101 | −2.19061 | −3.48521 | DOWN | 15 |
| A_33_P3349637, A_24_P234838\|5097 | 0 | −4.00838 | −3.4499 | −4.08292 | −4.13371 | −3.85649 | −3.97274 | DOWN | 16 |

Figure 24:
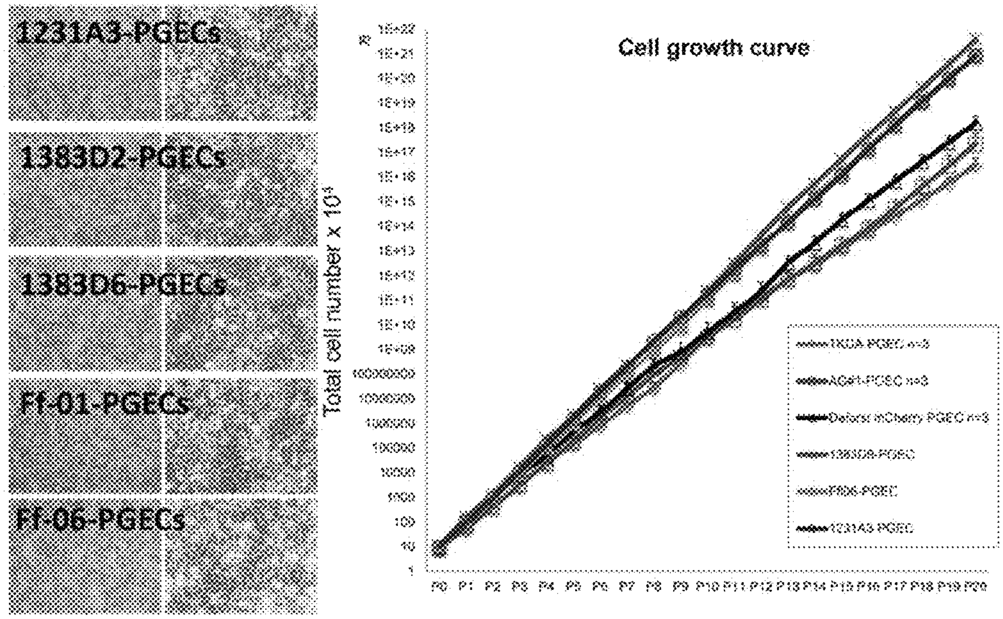
FIG. 24 depicts the establishment of primitive gut endoderm cells (PGECs) from various iPSC clones. A: Microscopic observation images of induced PGECs (day 5 of passage 0) from five different clones of iPS cells, 1231A3-, 1383D2-, 1383D6-, Ff-01- and Ff-06; B: Cell growth curve for each iPSC clone. PGECs derived from every clone could be passaged and amplified at least 20 times or more.

[Example 7] Establishment of Primitive Gut Endoderm Cells (PGECs) from Various iPS Clones (FIG. 24)

(Methods)

In addition to TkDA3-4 (the fourth clone of TkDA3 of Example 1 (as supplied from Tokyo University)), iPS cell clones such as 1231A3-, 1383D2-, 1383D6-, Ff-01- or Ff-06-[iPS cells cultured on iMatrix (laminin; purchased from Nippi, Inc.) (iPS cell clones established from peripheral blood by Kyoto University)] were used to prepare PGECs. For preparation of PGECs, the period of differentiation induction must be optimized for each clone. Method of induction is as summarized in Table 6.

TABLE 6

| Differentiation | TKDA | 1231A3/1383D2/1383D6/Ffl01/Ffl06 |
|---|---|---|
| Coating | Matrigel (growth factor reduced), RT, 2 hr | Laminin 511, 37° C., 3 hrs |
| D0 | In the presence of RPMI/1640, B27 (2%), Activin A (100 ng/ml) and Wnt3a (50 ng/ml), Rock Inhibitor (10 uM) | In the presence of RPMI/1640, B27 (2%), Activin A (100 ng/ml) and Wnt3a (50 ng/ml), Rock Inhibitor (10 uM) |
| D1 | In the presence of RPMI/1640, B27 (2%), Activin A (100 ng/ml) and Wnt3a (50 ng/ml) | In the presence of RPMI/1640, B27 (2%), Activin A (100 ng/ml) and Wnt3a (50 ng/ml) |
| D2 | In the presence of RPMI, B27 (2%), BMP4 (0.5 ng/ml), bFGF (5 ng/ml), VEGF (10 ng/ml) and Activin A (100 ng/ml) | In the presence of RPMI, B27 (2%), BMP4 (0.5 ng/ml), bFGF (5 ng/ml), VEGF (10 ng/ml) and Activin A (100 ng/ml) |
| D3 | In the presence of RPMI, B27 (2%), BMP4 (0.5 ng/ml), bFGF (5 ng/ml), VEGF (10 ng/ml) and Activin A (100 ng/ml) | In the presence of RPMI, B27 (2%), BMP4 (0.5 ng/ml), bFGF (5 ng/ml), VEGF (10 ng/ml) and Activin A (100 ng/ml) |
| D4 | In the presence of SFD and BMP4 (0.5 ng/ml), bFGF (5 ng/ml), VEGF (10 ng/ml) and Activin A (100 ng/ml) | In the presence of SFD and BMP4 (0.5 ng/ml), bFGF (5 ng/ml), VEGF (10 ng/ml) and Activin A (100 ng/ml) |
| D5 | In the presence of SFD and BMP4 (0.5 ng/ml), bFGF (5 ng/ml), VEGF (10 ng/ml) and Activin A (100 ng/ml) | Cells are differentiated by feeder-free culture and then passaged at least once. *Medium conditions: SFD, bFGF (5 ng/ml), VEGF (10 ng/ml), EGF (20 ng/ml), A83-01 (0.5 uM) and Chir99021 (3 uM) <Note> Cells are cultured in the presence of Rock Inhibitor only at the first stage (initial day). |
| Passage | Cells are differentiated by feeder-free culture and then passaged at least once. *Medium conditions: SFD, bFGF (5 ng/ml), VEGF (10 ng/ml), EGF (20 ng/ml), A83-01 (0.5 uM) and Chir99021 (3 uM) <Note> Cells are cultured in the presence of Rock Inhibitor only at the first stage (initial day). | |

(Results)

Microscopic views of induced primitive gut endoderm cells (passage 0, Day 5) are shown in FIG. 24A. For the induction, five different clones 1231A3-, 1383D2-, 1383D6-, Ff-01- and Ff-06- were used.

Cell growth curve for each iPS clone is shown in FIG. 24B. PGECs derived from every clone could be passaged and amplified for more than 20 times.

Figure 25:
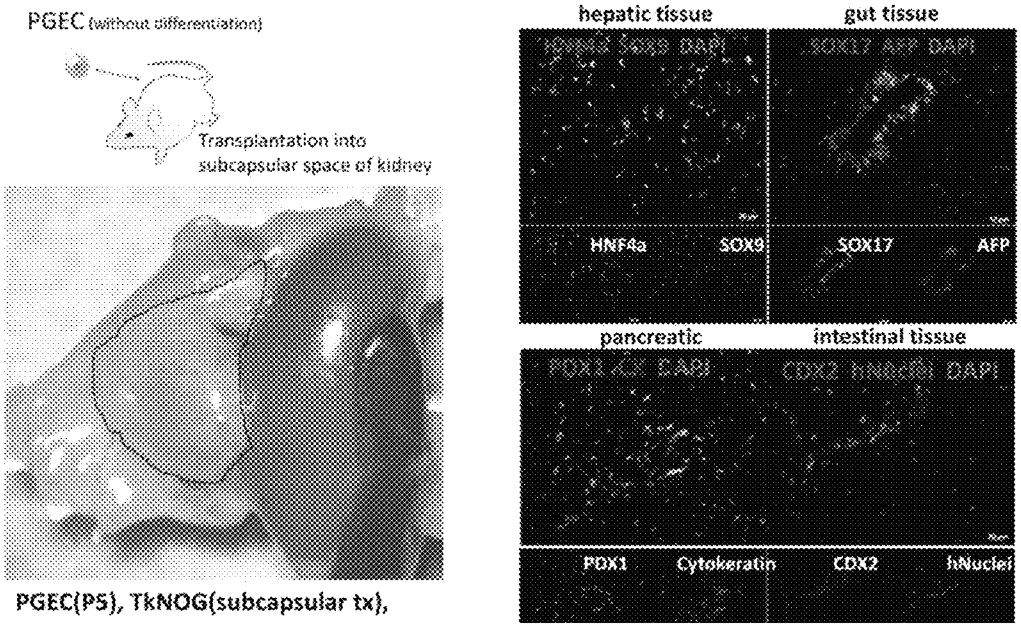
FIG. 25 depicts the ability of transplanted PGECs to reconstruct an endodermal tissue. A: Tissues were extracted one month after transplantation and no apparent formation of tumors such as teratoma or cancer was recognized. Black dotted line: PGEC-derived tissue. B: Immunohistochemical staining showed that PGEC-derived tissues formed various human endoderm-derived tissues, i.e., those tissues which are stained with markers of liver, pancreas and intestinal tract. Scale bar=50 μm.

[Example 8] Endodermal Tissue Reassembling Capacity of Transplanted PGECs (FIG. 25)

(Method)

One million PGECs prepared from iPS cell clone TkDA3-4 were transplanted into the subcapsular space of kidney in immunodeficient mice (TkNOG mice in which hepatic disorder had not been induced; Central Institute for Experimental Animals). The transplanted tissue was removed one month later, observed macroscopically and subjected to histological analysis.

(Results)

As a result of removal of tissues one month after transplantation, no apparent tumors such as teratoma or cancer were found to have formed (FIG. 25A). Black dotted line: PGEC-derived tissue.

As a result of immunohistochemical staining, PGEC-derived tissues formed various human endoderm-derived tissues (FIG. 25B). Briefly, the formation of tissues stained with liver/pancreas/intestinal tract markers was shown. Scale bar=50 μm

Figure 26:
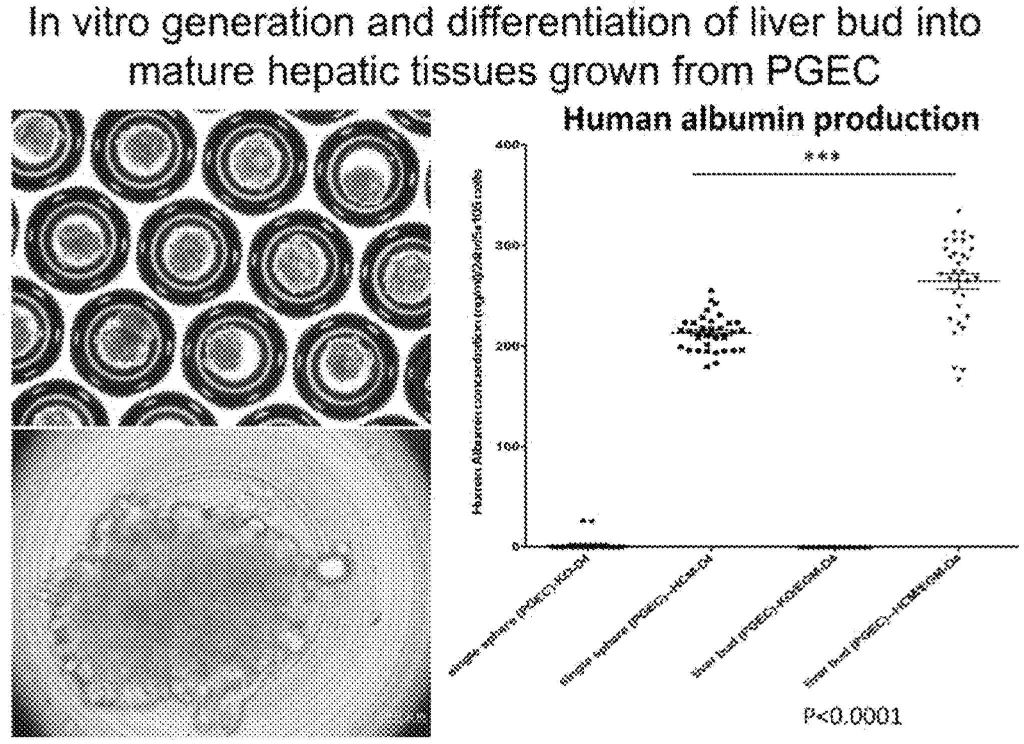
FIG. 26 illustrates function expression after long-term culture of PGEC-derived liver buds. A: Microscopic observations of PGEC-derived liver buds prepared in vitro. Scale bar=50 μm.

[Example 9] A Review of Functional Expression of PGEC-Derived Liver Buds after Long-Term Culture (FIG. 26)

(Method)

Liver buds were prepared from PGECs (Passage 5, Day 5) using culture plates of low adhesive property. For liver bud preparation, PGEC-derived cells, umbilical vein endothelial cells (HUVEC) and mesenchymal stem cells (MSC) were mixed at a ratio of 10:7:1 and subjected to differentiation and induction in a medium which was a 1:1 mixture of LONZA HCM medium and EGM medium. Albumin concentration in the culture supernatant of PGEC-derived liver buds after differentiation and induction was evaluated with an enzyme-linked immunosorbent assay (ELISA) quantification kit (Bethyl Laboratories Inc.).

(Results)

Microscopic views of PGEC-derived liver buds prepared in vitro are shown in FIG. 26A. Scale bar=50 μm Albumin secretion ability of PGEC-derived liver buds is shown in FIG. 26B. Human albumin was detected from day 4 of differentiation and induction using HCM/EGM. Further, when compared to tissues from a sphere culture of PGEC alone (i.e., tissues obtained by harvesting PGECs alone, plating at a density of $5\times10^5$ cells/well/24-well plate in low-adhesive culture plates with a shape in which cells gather at the bottom and culturing for several days), the PGEC-derived liver buds obviously showed a significantly high albumin secretion ability. When the medium condition was switched from HCM/EGM to KO-DMEM/EGM, albumin secretion was not confirmed.

[Example 10] Ammonia Metabolizing Function of Differentiated and Induced PGEC-Derived Liver Buds (FIG. 27)

(Method)

Liver buds derived from PGECs (P15) were differentiated and induced, and 2 mM $NH_4Cl$ was added to cell culture supernatant. Then, culture supernatant was collected at 0 hr, 3 hr, 6 hr and 24 hr, and ammonia concentration was measured with Ammonia Test (WAKO).

(Results)

It became clear that differentiated and induced PGEC-derived liver buds had a remarkable ammonia metabolizing function (FIG. 27).

[Example 11] Therapeutic Effect of PGEC-Derived Liver Buds Transplantation on Fulminant Liver Failure Model (FIG. 28)

(Method)

Diphtheria toxin (DT: Sigma, St. Louis, Mo., USA; D0564-1MG) was administered intraperitoneally into 8-week old Alb-TRECK/SCID mice (supplied from Tokyo Metropolitan Institute of Medical Science) (DT dose: 1.5 μg/kg). Subsequently, onset of fulminant liver failure was confirmed by finding that the AST value 48 hrs after administration was 8000 IU/L or more. Fulminant liver failure mouse individuals t satisfied this condition, PGEC spheres (n=9) or PGEC-derived liver buds (n=8) were transplanted under anesthesia into the subcapsular space of kidney. Transplantation groups and control group (non-transplantation group; Sham (n=13)) were compared for improvements in their survival ratios.

(Results)

It was revealed that the survival ratio of the groups transplanted with PGEC-derived spheres or liver buds was improved compared to that of non-transplanted group (FIG. 28).

[Example 12] Confirmation of Differentiation and Induction into Hepatocytes/Bile Duct Epithelial Cells by Immunohistochemical Staining (FIG. 29)

(Method)

PGEC-derived liver buds were transplanted into the subcapsular space of kidney in Alb-TRECK/SCID mice (the mice used in the experiment of FIG. 28). The resulting tissues were collected, macroscopically observed and histologically analyzed.

(Results)

PGEC-derived liver bud-transplanted tissues forming at one month after the transplantation were vascularized tissues. No findings were observed in which teratoma or malignant tumor was suspected (FIG. 29A).

The results of immunohistochemical staining revealed that liver tissues showing stainability for human nucleus specific antigen, human albumin (hepatocytes), human CK7 (bile duct epithelial cells) and human CD31 (blood vessels) had been formed (FIG. 29B). Scale bar=50 μm.

All publications, patents and patent applications cited herein are incorporated herein by reference in their entirety.

INDUSTRIAL APPLICABILITY

According to the present invention, organ cells for preparing tissues and organs can be prepared in high quality and in a stable manner. The technique of the present invention is applicable to drug discovery screening and regenerative medicine.

The invention claimed is:

1. Cells prepared by differentiating human pluripotent stem cells and then passaging the resultant cells at least once or more times, which are negative for undifferentiated cell markers NANOG, OCT4, MYC and LIN28A, negative for endoderm cell markers CXCR4, CER1, HHEX and GATA4, positive for intestinal endoderm cell markers CDX2 and HOXB9, negative for a mesenchymal cell marker brachyury (T), negative for a pancreatic cell marker PDX1, and capable of differentiating into at least hepatocytes, pancreatic cells and intestinal cells.

2. A method of preparing the resultant cells of claim 1, comprising culturing pluripotent stem cells without feeder cells in the presence of ROCK inhibitor, wherein said ROCK inhibitor is Y27632, at the first stage, in the presence of Activin A and Wnt3a at the second stage, in the presence of BMP4, bFGF, VEGF and Activin A at the third stage and in the presence of BMP4, bFGF, VEGF and Activin A at the fourth stage, to thereby effect differentiation and then passaging the resultant cells at least once or more times.

3. A method of amplifying the resultant cells of claim 1, comprising culturing the cells in the presence of ROCK inhibitor at the first stage after passage or on the first day of passage and thereafter in the presence of SFD, FGF2, VEGF, EGF, A83-01 and Chir99021.

4. A method of differentiating the resultant cells of claim 1, comprising:

directing differentiation and induction of the resultant cells into at least one of hepatocyte, pancreatic, or intestinal cells.

5. A method of constructing a working cell bank for preparing at least one of hepatocytes, pancreatic cells, and intestinal cells comprising:

cryopreserving the resultant cells of claim 1 at 1 to 20 passages.

* * * * *